US012570686B1

(12) United States Patent
Barbut et al.

(10) Patent No.: US 12,570,686 B1
(45) Date of Patent: Mar. 10, 2026

(54) CHEMICAL STRUCTURES THAT CONTROL METABOLIC ELIMINATION OF AMINOSTEROLS

(71) Applicant: BAZ Therapeutics, Inc., Philadelphia, PA (US)

(72) Inventors: Denise Barbut, Philadelphia, PA (US); Michael Zasloff, Philadelphia, PA (US)

(73) Assignee: BAZ Therapeutics, Inc., Philadelphia, PA (US)

( * ) Notice: Subject to any disclaimer, the term of this patent is extended or adjusted under 35 U.S.C. 154(b) by 0 days.

(21) Appl. No.: 19/056,358

(22) Filed: Feb. 18, 2025

Related U.S. Application Data

(63) Continuation of application No. PCT/US2024/056173, filed on Nov. 15, 2024.

(51) Int. Cl.

| | |
|---|---|
| ***C07J 41/00*** | (2006.01) |
| ***A61K 9/00*** | (2006.01) |
| ***A61K 9/08*** | (2006.01) |
| ***A61K 31/575*** | (2006.01) |
| ***A61K 47/02*** | (2006.01) |
| ***A61K 47/40*** | (2006.01) |
| ***A61P 3/04*** | (2006.01) |

(52) U.S. Cl.
CPC ......... *C07J 41/0005* (2013.01); *A61K 9/0019* (2013.01); *A61K 9/08* (2013.01); *A61K 31/575* (2013.01); *A61K 47/02* (2013.01); *A61K 47/40* (2013.01); *A61P 3/04* (2018.01)

(58) Field of Classification Search
CPC ... C07J 41/0005; A61K 9/0019; A61K 31/575
See application file for complete search history.

(56) References Cited

U.S. PATENT DOCUMENTS

| | | | |
|---|---|---|---|
| 7,557,097 | B2 | 7/2009 | Sorensen et al. |
| 2020/0262864 | A1 | 8/2020 | Barbut et al. |
| 2021/0260078 | A1 | 8/2021 | Zasloff et al. |
| 2023/0123701 | A1 | 4/2023 | Barbut et al. |
| 2023/0125585 | A1 | 4/2023 | Barbut et al. |
| 2023/0174988 | A1 | 6/2023 | Devlin et al. |

FOREIGN PATENT DOCUMENTS

| | | | |
|---|---|---|---|
| WO | WO-9726888 | A1 | 7/1997 |
| WO | WO-02006299 | A2 | 1/2002 |
| WO | WO-2006055009 | A1 | 5/2006 |
| WO | WO-2021025973 | A1 | 2/2021 |
| WO | WO-2024006288 | A1 | 1/2024 |

OTHER PUBLICATIONS

Zasloff et al.; "A spermine-coupled cholesterol metabolite from the shark with potent appetite suppressant and antidiabetic properties"; 2001; International Journal of Obesity; 25:689-697 (Year: 2001).*

(Continued)

*Primary Examiner* — Timothy P Thomas

(74) *Attorney, Agent, or Firm* — Wilson Sonsini Goodrich & Rosati

(57) ABSTRACT

Provided herein are aminosterol compounds with modified pharmacokinetic profiles. Also provided herein are methods of treating disease, such as obesity, equine laminitis, equine metabolic syndrome, or cancer with the aminosterol compounds.

6 Claims, 14 Drawing Sheets

(56) References Cited

OTHER PUBLICATIONS

Yale; "The Trifluoromethyl Group in Medicinal Chemistry"; Journal of Medicinal and Pharmaceutical Chemistry; 1959; 1(2): 121-133 (Year: 1957).*
Kazakova, Oxana. et al. From Marine Metabolites to the Drugs of the Future: Squalamine, Trodusquemine, Their Steroid and Triterpene Analogues. International journal of molecular sciences 23(3):1075, 1-54 (2022).
Park, Kevin B. et al. Metabolism of fluorine-containing drugs. Annual review of pharmacology and toxicology 41:443-470 (2001).
PCT/US2024/056173 International Search Report and Written Opinion dated Mar. 19, 2025.
PCT/US2024/056173 Invitation to Pay Additional Fees dated Jan. 14, 2025.
Salmi, Chanaz. et al. New stereoselective titanium reductive amination synthesis of 3-amino and polyaminosterol derivatives possessing antimicrobial activities. European journal of medicinal chemistry 43(3):540-547 (2008).
Barbut, Denise et al. Anti-aging properties of the aminosterols of the dogfish shark. npj Aging 10(62):1-10 (2024).
Bourebaba, Lynda et al. The PTP1B inhibitor MSI-1436 ameliorates liver insulin sensitivity by modulating autophagy, ER stress and systemic inflammation in Equine metabolic syndrome affected horses. Frontiers in Endocrinology 14(1149610): (2023).
Ellis, Jim. Multiple Doses of Trodusquemine Improve Glucose Tolerance in Type 2 Diabetic Subjects. American Diabetes Association, 69th Scientific Sessions, Abstract No. 2071-PO (2009).
Krishnan et al., Targeting the disordered C terminus of PTP1B with an allosteric inhibitor. Nat Chem Biol. 10(7): 558-566 (2014).
Lantz, K. A., Inhibition of PTP1B by Trodusquemine (MSI-1436) Causes Fat-specific Weight Loss in Diet-induced Obese Mice. Obesity, Aug. 2010;18(8):1516-1523. doi: 10.1038/oby.2009.444. Epub Jan. 14, 2010.
Trodusquemine, Cognitive Vitality Report®, Alzheimer's Drug Discovery Foundation, Apr. 18, 2019.
Ahima, Rexford S. et al. Appetite Suppression and Weight Reduction by a Centrally Active Aminosterol. Diabetes 51(7):2099-2104 (2002).
Bourebaba, Lynda. et al. MSI-1436 improves EMS adipose derived progenitor stem cells in the course of adipogenic differentiation through modulation of ER stress, apoptosis, and oxidative stress. Stem Cell Research & Therapy 12(1):97, 1-18 (2021).
Bourebaba, Lynda. et al. The PTP1B Inhibitor Trodusquemine (MSI-1436) Improves Glucose Uptake in Equine Metabolic Syndrome Affected Liver through Anti-Inflammatory and Antifibrotic Activity. International Journal of Inflammation 2023, 3803056:1-22 (2023).
Bourebaba, Lynda. et al. The PTP1B selective inhibitor MSI-1436 mitigates Tunicamycin-induced ER stress in human hepatocarcinoma cell line through XBP1 splicing modulation. PlosOne 18(1):e0278566, 1-16 (2023).
Colman, Ricki J. et al. Caloric restriction delays disease onset and mortality in rhesus monkeys. Science 325(5937):201-204 (2009).
Liu, Feng. et al. PTP1B Inhibition Improves Mitochondrial Dynamics to Alleviate Calcific Aortic Valve Disease Via Regulating OPA1 Homeostasis. JACC. Basic to translational science 7(7):697-712 (2022).
Merry, B J, and A M Holehan. Onset of puberty and duration of fertility in rats fed a restricted diet. Journal of Reproduction and Fertility 57(2):253-259 (1979).
Pandey, Nihar R. et al. LMO4 is required to maintain hypothalamic insulin signaling. Biochemical and Biophysical Research Communications 450(1):666-672 (2014).
Perni, Michele. et al. A natural product inhibits the initiation of a-synuclein aggregation and suppresses its toxicity. Proceedings of the National Academy of Sciences of the United States of America 114(6):E1009-E1017 (2017).
Perni, Michele. et al. Multistep Inhibition of a-Synuclein Aggregation and Toxicity in Vitro and in Vivo by Trodusquemine. ACS Chemical Biology 13(8):2308-2319 (2018).
Qin, Zhaohong. et al. Chronic stress induces anxiety via an amygdalar intracellular cascade that impairs endocannabinoid signaling. Neuron 85(6):1319-1331 (2015).
Ricke, Konrad M. Neuronal Protein Tyrosine Phosphatase 1B Hastens Amyloid beta-Associated Alzheimer's Disease in Mice. The Journal of Neuroscience 40(7):1581-1593 (2020).
Smith, Ashley M. et al. The protein tyrosine phosphatase 1B inhibitor MSI-1436 stimulates regeneration of heart and multiple other tissues. NPJ Regenerative medicine 3(1):1-10 (2017).
Takahashi, Nobuhiko. et al. A novel aminosterol reverses diabetes and fatty liver disease in obese mice. Journal of Hepatology 41(3):391-398 (2004).
Thiebaut, Pierre-Alain. et al. Protein tyrosine phosphatase 1B regulates endothelial endoplasmic reticulum stress; role in endothelial dysfunction. Vascular Pharmacology 109:36-44 (2018).
Thompson, Dawn. et al. Pharmacological inhibition of protein tyrosine phosphatase 1B protects against atherosclerotic plaque formation in the LDLR-/- mouse model of atherosclerosis. Clinical science 131(20):2489-2501 (2017).
Turturro, Angelo. et al. Growth Curves and Survival Characteristics of the Animals Used in the Biomarkers of Aging Program. J Gerontol A Biol Sci Med Sci. 54(11):B492-B501 (1999).
Wiede, Florian. et al. PTP1B Is an Intracellular Checkpoint that Limits T-cell and CAR T-cell Antitumor Immunity. Cancer discovery 12(3):752-773 (2022).
Zasloff, M. et al. A spermine-coupled cholesterol metabolite from the shark with potent appetite suppressant and antidiabetic properties. International Journal of Obesity and Related Metabolic Disorders 25(5):689-697 (2001).
Zhang, Li. et al. Tyrosine phosphatase PTP1B impairs presynaptic NMDA receptor-mediated plasticity in a mouse model of Alzheimer's disease. Neurobiology of disease 156:105402, 1-13 (2021).

* cited by examiner

FIG. 8H
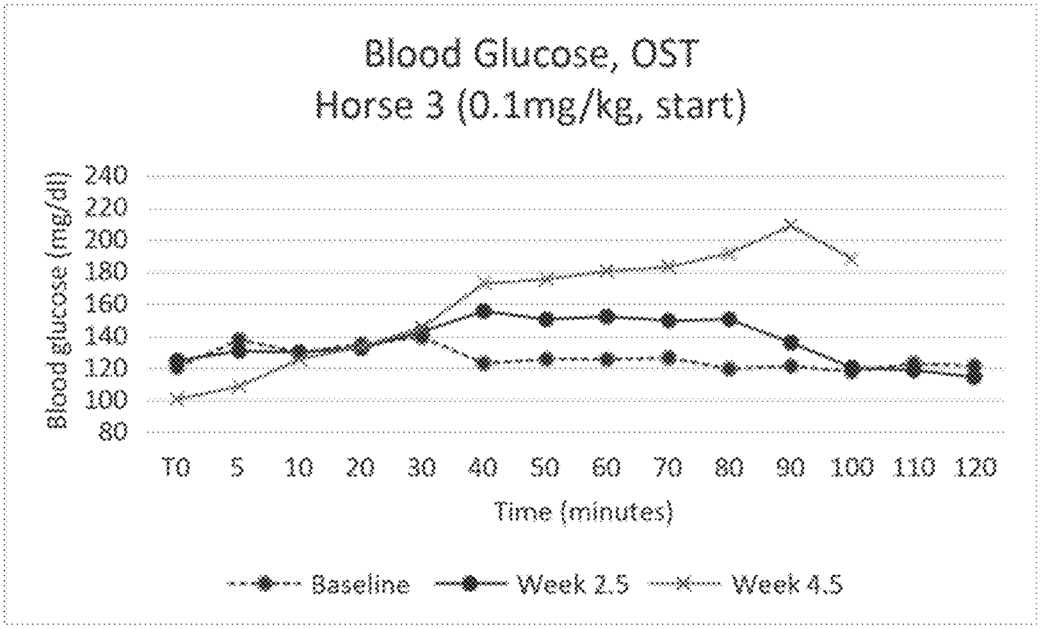
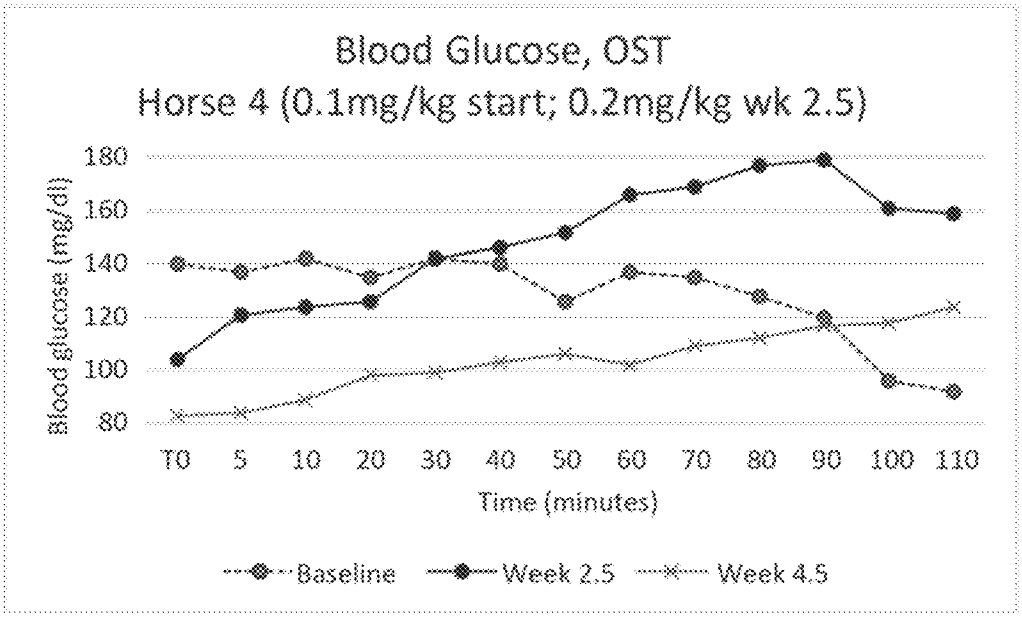
FIG. 8I

CHEMICAL STRUCTURES THAT CONTROL METABOLIC ELIMINATION OF AMINOSTEROLS

CROSS-REFERENCE

This application is a continuation of International Patent Application No. PCT/US2024/056173, filed Nov. 15, 2024, which is incorporated herein by reference in its entirety.

BACKGROUND

Aminosterols are metabolites of cholesterol containing a polyamine substituent. It is challenging to identify modifications to aminosterol compounds that improve their pharmacokinetic properties while maintaining the biological activities of the parent compound. Accordingly, there is a need to develop aminosterol compounds with improved pharmacokinetic half-life and potency to enable development of this class of molecules into drugs.

SUMMARY

Provided herein, in some embodiments, are aminosterol compounds with improved pharmacokinetic half-life and potency. Provided herein, in some embodiments, are aminosterol compounds that are safe for administration to mammals and possess improved pharmacokinetic half-life compared to natural aminosterols (such as Trodusquemine). Also provided herein are methods for manufacturing aminosterol compounds that can improve the pharmacological potency and/or pharmacokinetic half-life as compared to the parent compounds, and in particular without modifying the intended pharmacological activity of the parent compounds. Methods for using the compounds described herein are also provided, such as for treatment of diseases including equine metabolic syndrome, equine laminitis, obesity, and canine cancers.

Provided herein, in some embodiments, is a compound of Formula (I):

Formula (I)

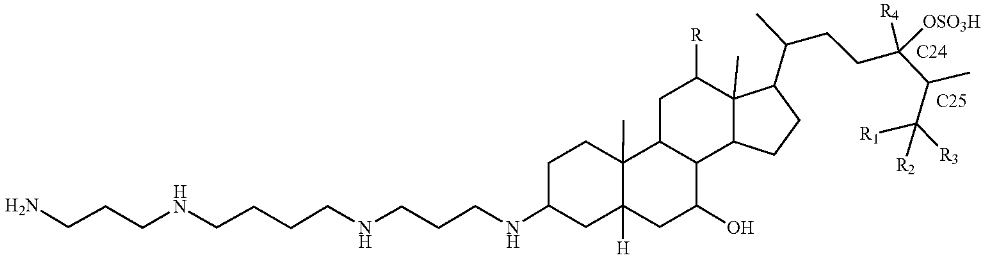

wherein,

R is hydrogen or hydroxyl:

$R_1$, $R_2$ and $R_3$ are each independently selected from hydrogen, F, and $C_1$-$C_3$ alkyl: and $R_4$ is hydrogen or $CH_2OH$, wherein at least one of $R_1$, $R_2$ and $R_3$ is, F, or $C_1$-$C_3$ alkyl, or a pharmaceutically acceptable salt, ester, or stereoisomer thereof.

In some embodiments, the compound of Formula (I) is of Formula (Ia):

Formula (Ia)

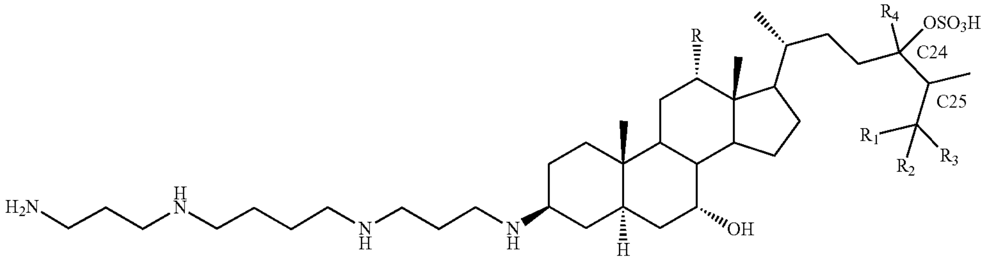

or a pharmaceutically acceptable salt, ester, or stereoisomer thereof.

In some embodiments, R is hydrogen. In some embodiments, $R_4$ is hydrogen.

In some embodiments, the compound of Formula (I) is of Formula (II):

Formula (II)

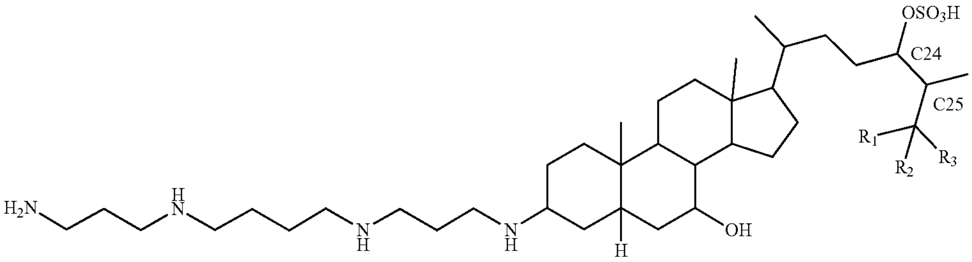

or a pharmaceutically acceptable salt, ester, or stereoisomer thereof.

In some embodiments, the compound of Formula (I) is of Formula (IIa):

Formula (IIa)

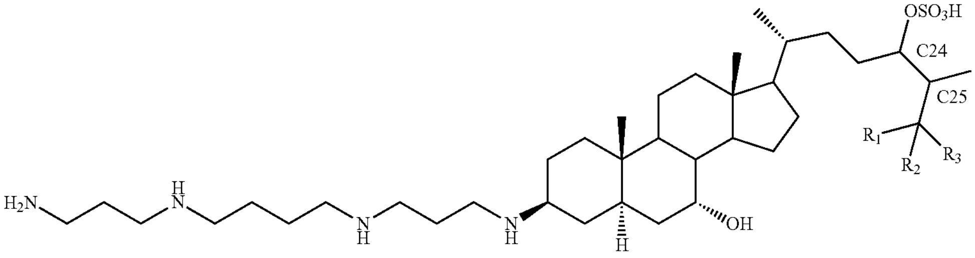

or a pharmaceutically acceptable salt, ester, or stereoisomer thereof.

In some embodiments, at least one of $R_1$, $R_2$, and $R_3$ is $C_1$-$C_3$ alkyl. In some embodiments, at least one of $R_1$, $R_2$, and $R_3$ is methyl. In some embodiments, at least one of $R_1$, $R_2$, and $R_3$ is F. In some embodiments, at least one of $R_1$, $R_2$, and $R_3$ is hydrogen.

In some embodiments, the compound is:

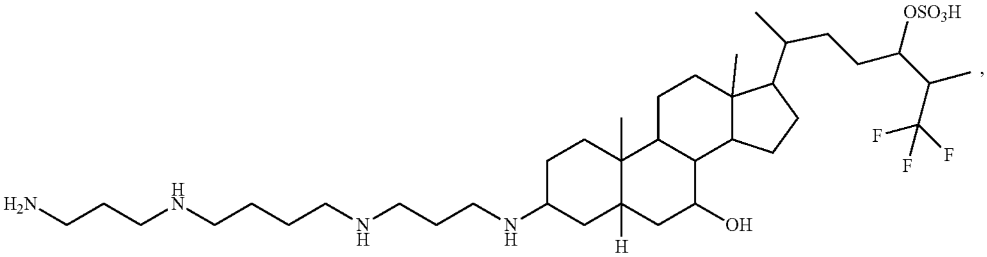

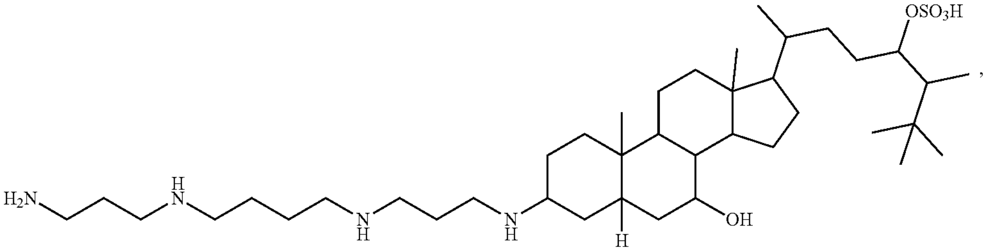

-continued
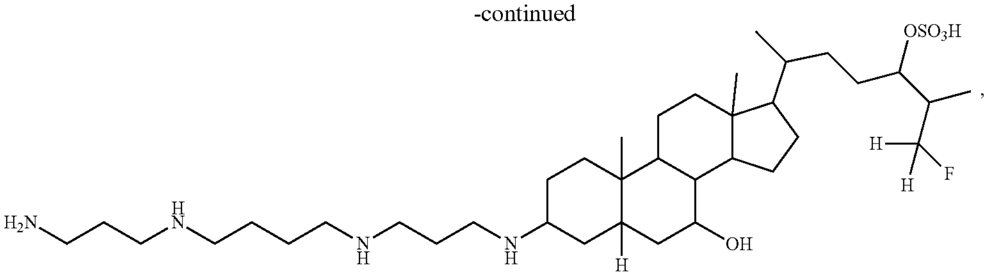
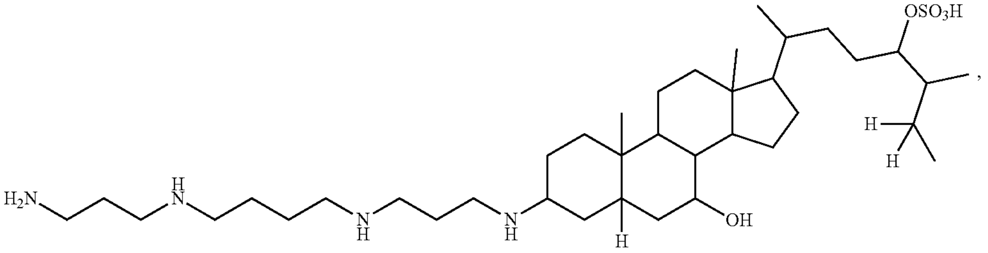
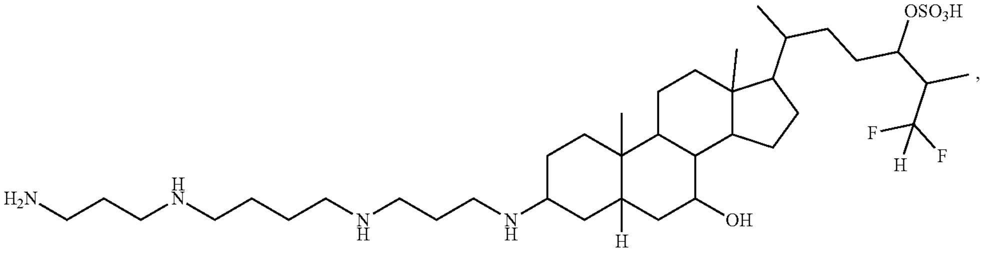
and
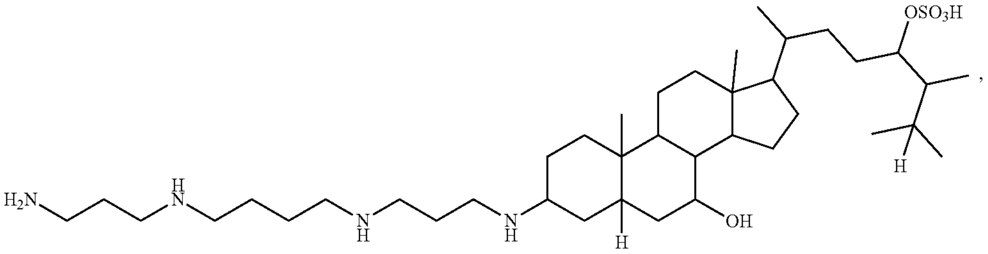
or a pharmaceutically acceptable salt, ester, or stereoisomer thereof.
In some embodiments, C24 is in the(S) orientation. In some embodiments, the compound of Formula (II) is of Formula (IIb):
Formula (IIb)
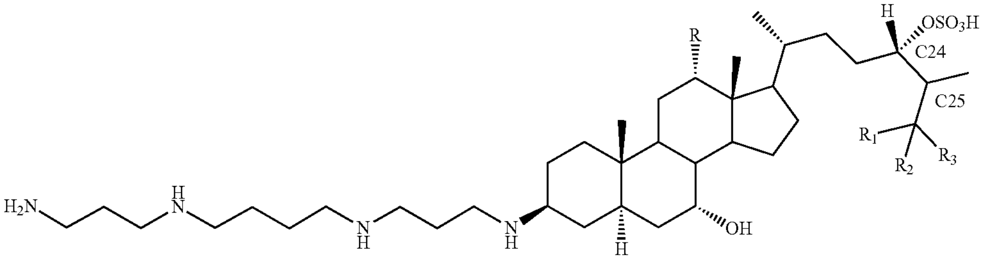

or a pharmaceutically acceptable salt, ester, or stereoisomer thereof.

In some embodiments, C24 is in the (R) orientation. In some embodiments, the compound of Formula (II) is of Formula (IIc):

Formula (IIc)

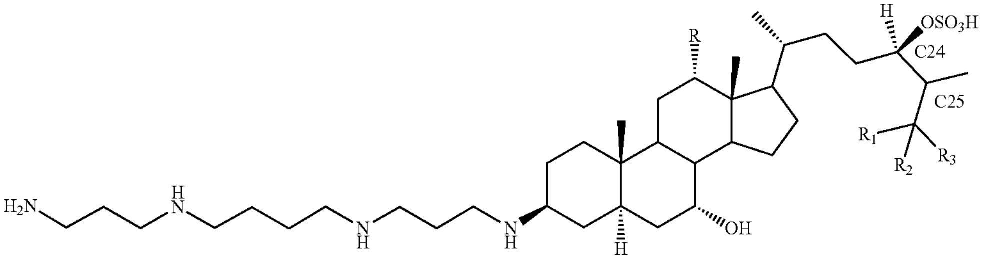

or a pharmaceutically acceptable salt, ester, or stereoisomer thereof.

In some embodiments, C25 is in the(S) orientation. In some embodiments, C25 is in the (R) orientation.

In some embodiments, the compound is:

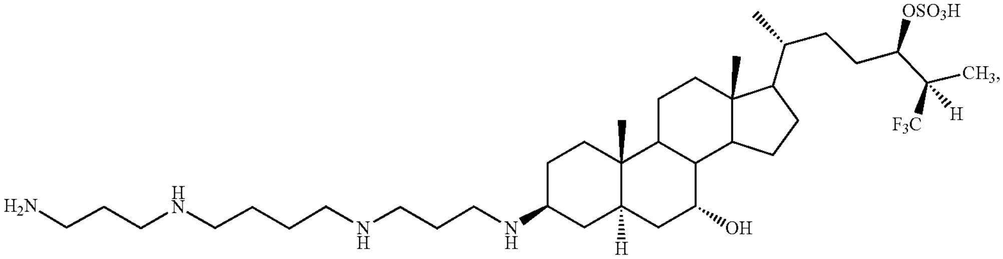

,

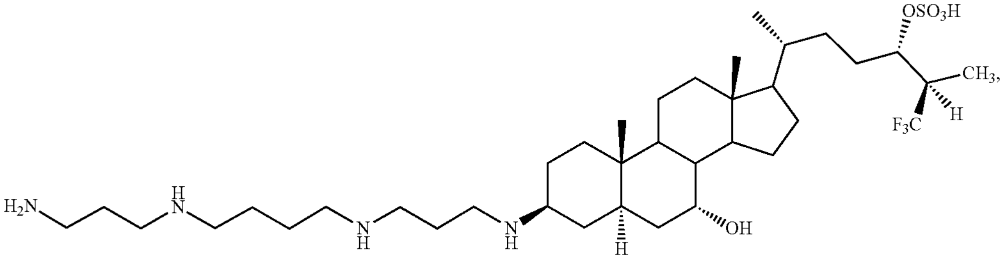

,

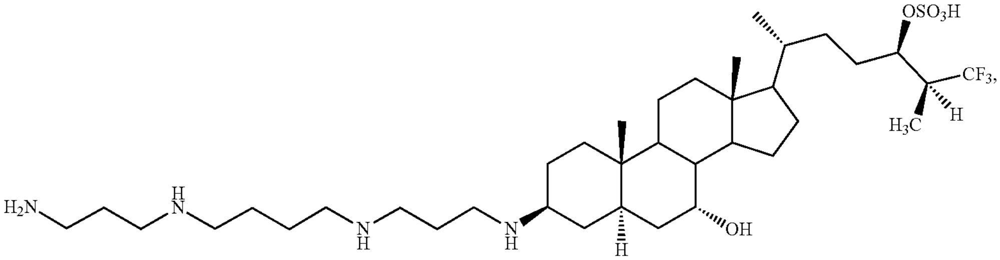

, and

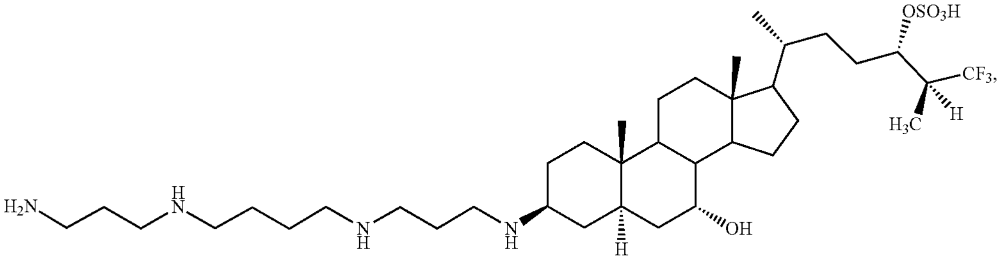

, or a pharmaceutically acceptable salt, ester, or stereoisomer thereof.

In some embodiments, $R_4$ is $CH_2OH$. In some embodiments, the compound of Formula (I) is of Formula (III):

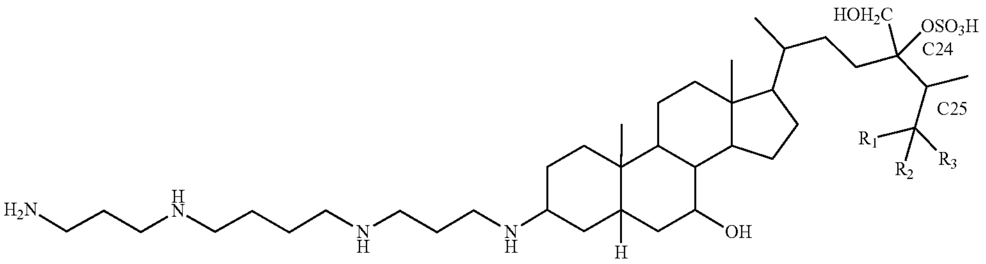
Formula (III)

or a pharmaceutically acceptable salt, ester, or stereoisomer thereof.

In some embodiments, the compound of Formula (I) is of Formula (IIIa):

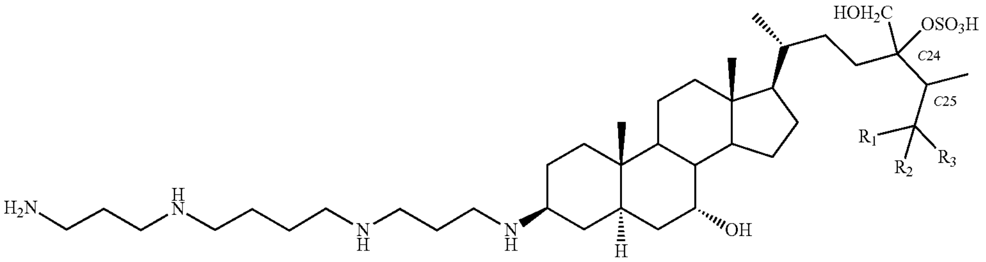
Formula (IIIa)

or a pharmaceutically acceptable salt, ester, or stereoisomer thereof.

In some embodiments, the compound of Formula (I) is of Formula (IV):

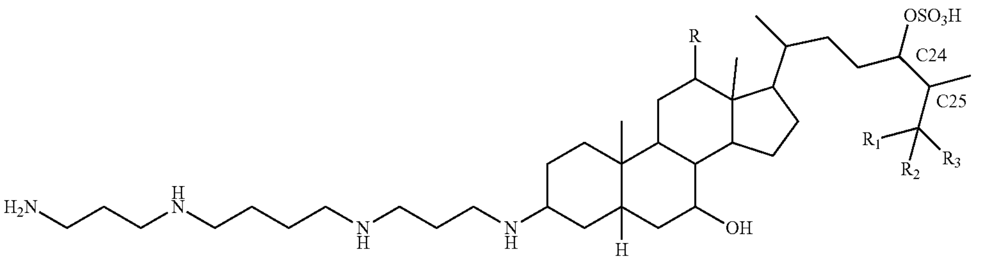
Formula (IV)

or a pharmaceutically acceptable salt, ester, or stereoisomer thereof.

In some embodiments, the compound of Formula (I) is of Formula (IVa):

Formula (IVa)

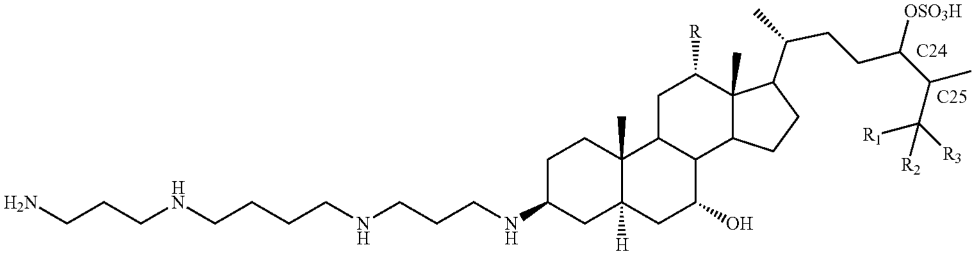

or a pharmaceutically acceptable salt, ester, or stereoisomer thereof.

Provided herein in some embodiments, is a compound or a pharmaceutically acceptable salt, ester, or stereoisomer thereof, wherein the compound is:

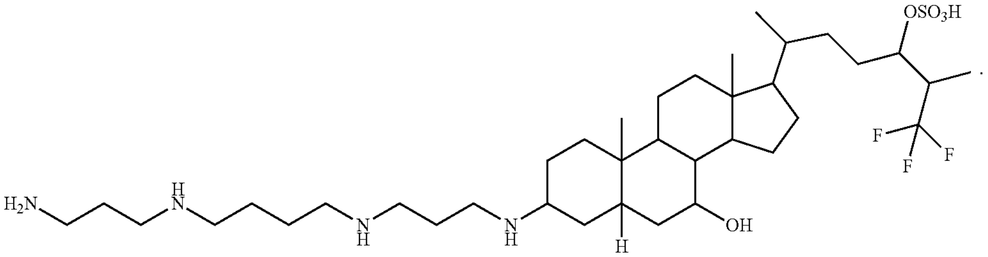

In some embodiments, the compound is:

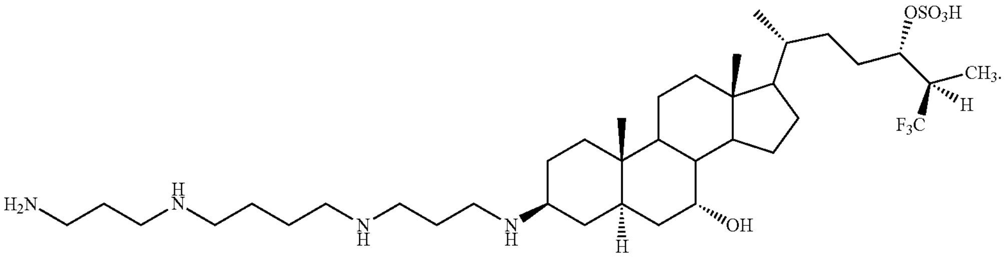

In some embodiments, provided herein is a pharmaceutical composition comprising any one of the compounds provided herein and a pharmaceutically acceptable excipient. In some embodiments, the composition has a stereochemical purity of at least 90%. In some embodiments, the composition has a stereochemical purity of at least 95%. In some embodiments, the pharmaceutical composition further comprises a buffering agent, solubilizing agent, carrier, excipient, binder, filler, diluent, disintegrant, wetting agent, lubricant, glidant, coloring agent, dye migration inhibitor, sweetening agent, flavoring agent or a combination thereof. In some embodiments, the pharmaceutical composition comprises the compound in an amount of from about 5 mg/mL to about 50 mg/mL. In some embodiments, the pharmaceutical composition comprises the solubilizing agent in an amount of from about 80 mg/mL to about 250 mg/mL. In some embodiments, the pharmaceutical composition comprises the buffering agent in an amount of from about 20 mM to about 80 mM. In some embodiments, the pharmaceutical composition comprises: (a) the compound in an amount of from about 5 mg/mL to about 50 mg/mL: (b) a solubilizing agent in an amount of from about 80 mg/mL to about 250 mg/mL; and (c) a buffering agent in an amount of from about 20 mM to about 80 mM. In some embodiments, the pharmaceutical composition comprises: (a) the compound in an amount of about 10 mg/mL: (b) 2-hydroxypropyl β-cyclodextrin in an amount of about 100 mg/mL; and (c) about 30 mM of phosphate buffer. In some embodiments, the pharmaceutical composition is formulated for subcutaneous administration.

In some embodiments, provided herein is a method of treating a disease in a subject in need thereof, the method comprising administering to the subject a therapeutically effective amount of any one of the compounds provided herein or any pharmaceutical composition provided herein. In some embodiments, the method comprises use of a dosing regimen. In some embodiments, the dosing regimen is determined and/or adjusted on the basis of at least one metabolic parameter selected from body weight, blood glucose, blood HBA1c, triglycerides and/or insulin. In some embodiments, the method comprises monitoring the effect of treatment using symptoms and biomarkers. In some embodiments, the disease is a metabolic disease. In some embodiments, the metabolic disease is equine metabolic syndrome. In some embodiments, the metabolic disease is equine laminitis. In some embodiments, the metabolic disease is obesity (e.g., in a dog or in a horse). In some embodiments, the disease is an age-related disease. In some embodiments, the age-related disease is an age-related neurodegenerative disease. In some embodiments, the disease is cancer. In some embodiments, the compound or pharmaceutical composition is administered orally, intravenously, subcutaneously, intranasally, intrathecally, or a combination thereof. In some embodiments, the compound or pharmaceutical composition is administered intravenously. In some embodiments, the compound or pharmaceutical composition is administered subcutaneously. In some embodiments, the subject is a mammal. In some embodiments, the mammal is non-human mammal. In some embodiments, the non-human mammal is a dog. In some embodiments, the non-human mammal is a horse. In some embodiments, the mammal is human. In some embodiments, the compound is administered in an amount of about 5-50 mg (e.g, about 5 mg, about 20 mg, about 25 mg, about 30 mg, about 35 mg, about 40 mg, or about 50 mg.). In some embodiments, the compound is administered in an amount of about 25-35 mg. In some embodiments, the compound is administered in an amount of about 0.02-0.10 mg/kg (e.g., about 0.02 mg/kg, about 0.03 mg/kg, about 0.04 mg/kg, about 0.05 mg/kg, about 0.06 mg/kg, about 0.07 mg/kg, or about 0.08 mg/kg). In some embodiments, the compound is administered in an amount of about 0.1-10 mg/kg (e.g., about 0.1 mg/kg, about 0.5 mg/kg, about 2.5 mg/kg, or about 5 mg/kg). In some embodiments, the compound is administered in a single dose. In some embodiments, the compound is administered in a single dose every 2-6 weeks. In some embodiments, the compound is administered every 4 weeks.

In some embodiments, provided herein is a composition for use in the treatment of a disease comprising any compound provided herein or any pharmaceutical composition provided herein. In some embodiments, the disease is a metabolic disease. In some embodiments, the metabolic disease is equine metabolic syndrome. In some embodiments, the metabolic disease is equine laminitis. In some embodiments, the metabolic disease is obesity (e.g., in a dog or in a horse). In some embodiments, the disease is an age-related disease. In some embodiments, the age-related disease is an age-related neurodegenerative disease. In some embodiments, the disease is cancer.

In some embodiments, provided herein is a method of manufacturing a compound of Formula (I), or a pharmaceutically acceptable salt, ester, or stereoisomer thereof, Formula (I)

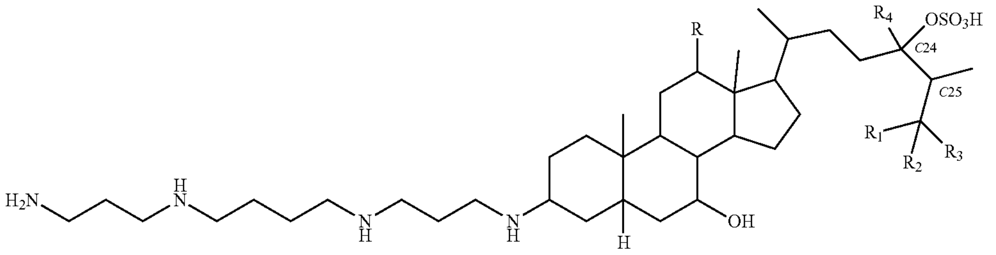

wherein,

R is hydrogen or hydroxyl:

$R_1$, $R_2$ and $R_5$ are each independently selected from hydrogen, F, and $C_1$-$C_3$ alkyl: and $R_4$ is hydrogen or $CH_2OH$:

wherein at least one of $R_1$, $R_2$ and $R_3$ is, F, or $C_1$-$C_3$ alkyl, wherein the method comprises:

(a) providing a compound of Formula (X), or a stereoisomer thereof:

Formula (X)

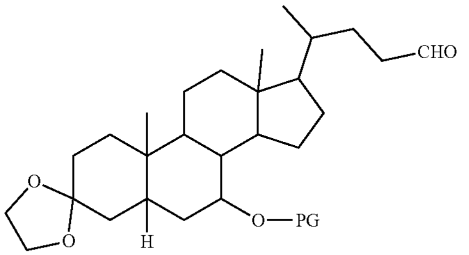

wherein PG is an alcohol protecting group;

(b) contacting the compound of Formula (X) with

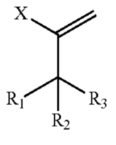

to provide a compound of Formula (Z), or a stereoisomer thereof:

Formula (Z)

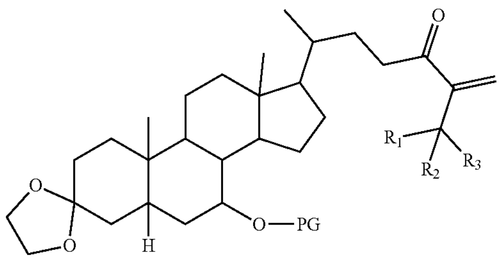

wherein,

X is a halogen;

$R_1$, $R_2$ and $R_3$ are each independently selected from hydrogen, F, and $C_1$-$C_3$ alkyl;

(c) processing the compound of Formula (Z) to provide a compound of Formula (W):

Formula (W)

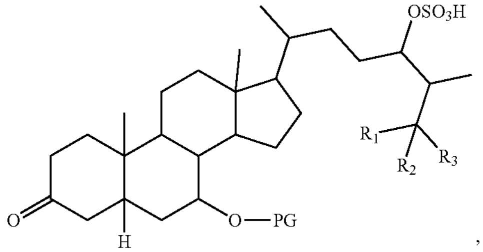

, and (d) contacting the compound of Formula (W) with a spermine (e.g., protected spermine).

In some embodiments, processing comprises reducing, deprotecting and sulfonylating. In some embodiments, reducing comprises stereospecific reduction. In some embodiments, the reducing comprises use of a chiral reducing reagent. In some embodiments, the stereospecific reduction comprises use of (R,R)-Ts-DENEB. In some embodiments, the deprotecting in (c) comprises acetonide deprotection. In some embodiments, the deprotecting in (c) comprises use of an acid. In some embodiments, the spermine is a protected spermine (e.g., CBz-spermine). In some embodiments, the method further comprises deprotecting the protected spermine. In some embodiments, the deprotecting of the spermine comprises use of a base. In some embodiments, the method further comprises a deprotecting step that replaces the protecting group PG with a hydrogen.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the features and advantages of the present disclosure may be obtained by reference to the following detailed description that sets forth illustrative embodiments, in which the principles of the disclosure are utilized, and the accompanying drawings (also "Figure" and "FIG." herein), of which:

FIG. 1 shows the chemical structure of Compound 1a.

FIG. 8F, FIG. 8G, FIG. 8H, and FIG. 8I show blood glucose levels in horses after administration of a compound provided herein.

DETAILED DESCRIPTION

Certain Definitions

Figure 1:
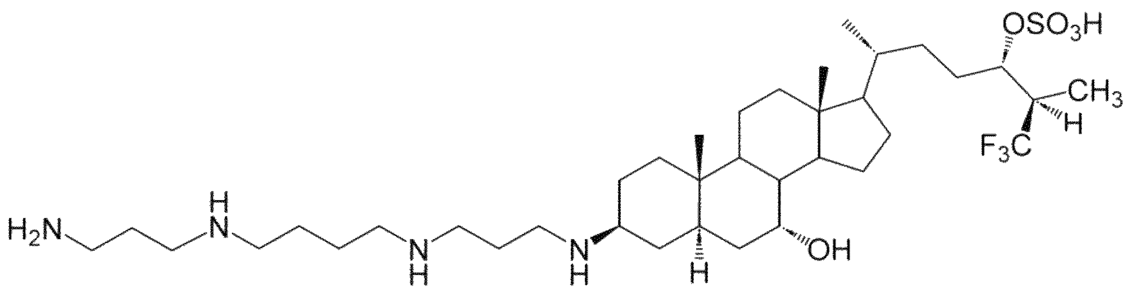

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included.

The term "about" when referring to a number or a numerical range means that the number or numerical range referred to is an approximation within experimental variability (or within statistical experimental error), and thus the number or numerical range may vary up to ±1%, up to ±5%, up to ±10%, or up to ±15% of the stated number or numerical range.

The terms "comprise", "have", and "include" are open-ended linking verbs. Any forms or tenses of one or more of these verbs "comprises," "comprising," "has," "having," "includes," and "including" are also open-ended. For example, any method that "comprises," "has" or "includes" one or more steps is not limited to possessing only those one or more steps and also covers other unlisted steps.

The terms “treat,” “treating,” or “treatment” as used herein, include reducing, alleviating, abating, ameliorating, managing, relieving, or lessening the symptoms associated with a disease, disease state, condition, or indication in either a chronic or acute therapeutic scenario. Also, treatment of a disease or disease state described herein includes the disclosure of use of such compound or composition for the treatment of such disease, disease state, disorder, or indication.

“Hydroxyl” refers to the —OH radical.

“Alkyl” refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as “$C_1$-$C_6$ alkyl” or “$C_{1-6}$alkyl”, means that the alkyl group may consist of 1 carbon atom, 2 carbon atoms, 3 carbon atoms, 4 carbon atoms, 5 carbon atoms or 6 carbon atoms, although the present definition also covers the occurrence of the term “alkyl” where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —$NH_2$, or —$NO_2$. In some embodiments, the alkyl is optionally substituted with halogen, —CN, —OH, or —OMe. In some embodiments, the alkyl is optionally substituted with halogen.

“Pharmaceutically acceptable salt” includes both acid and base addition salts. A pharmaceutically acceptable salt of any one of the pharmacological agents described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

“Pharmaceutically acceptable acid addition salt” refers to those pharmaceutically acceptable salts, which are formed with inorganic acids such as hydrochloric acid, hydrobromic acid, sulfuric acid, nitric acid, phosphoric acid, hydroiodic acid, hydrofluoric acid, phosphorous acid, and the like, or formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example. Berge S. M. et al., “Pharmaceutical Salts.” *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

“Pharmaceutically acceptable base addition salt” refers to pharmaceutically acceptable salts that are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

Aminosterol Compounds

In some embodiments, provided herein are aminosterol compounds with improved pharmacokinetic half-life and/or potency as compared to their parent compounds. The location and identity of structural modification may be important features of the aminosterol compounds described herein. The chemical structure of the parent aminosterol compounds may be modified in such a way as to hinder metabolic destruction of the compounds while preserving the desired pharmacological characteristics of the compounds.

A series of aminosterols are isolatable from the liver of the dogfish shark, including Trodusquemine. In some instances, these aminosterols are known to exhibit anti-microbial activities.

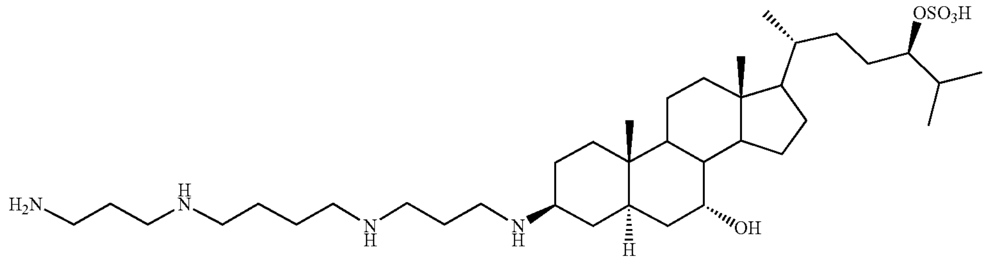

Trodusquemine (MSI-1436)

The pharmacokinetic half-life of a drug may represent a desirable characteristic of a therapeutic. In some cases, the half-life determines how much of an administered drug will be exposed to the tissues of the subject over a period of time following dosing. Generally, the longer the half-life, the greater the exposure; and the greater the exposure, the more effective the treatment. As a consequence, the pharmacokinetic half-life may determine both the amount of a drug that must be administered to achieve a therapeutic effect as well as the frequency that the drug must be administered. A drug with a half-life of minutes may need to be administered continuously whereas a drug with a half-life of days may in some instances be administered once every few days or weekly, as an example.

The aminosterol described hereinabove poses a specific challenge with respect to the introduction of modifications of the chemical structure that might extend the pharmacological half-life. These compounds bind to cellular membranes and interact with many unknown targets in ways that remain largely unknown. In some cases, minor modifications can completely alter their pharmacology. This may result in challenges when attempting to modify such aminosterol compounds to, for instance, increase pharmacological half-life. Provided herein are modified aminosterol compounds which have increased pharmacological half-life, with modifications that preserve the biological activity of the original compounds.

Provided here in some embodiments, are modified versions of Trodusquemine, such as analogs of Trodusquemine that maintain the pharmacological function of Trodusquemine while modifying the pharmacokinetic properties of Trodusquemine.

In some embodiments, provided herein is a compound of Formula (I), or a pharmaceutically acceptable salt, ester, or stereoisomer thereof:

wherein,

R is hydrogen or hydroxyl:

$R_1$, $R_2$ and $R_5$ are each independently selected from hydrogen, F, and $C_1$-$C_3$ alkyl: and $R_4$ is hydrogen or $CH_2OH$, wherein at least one of $R_1$, $R_2$ and $R_3$ is, F, or $C_1$-$C_3$ alkyl.

In some embodiments, the compound of Formula (I) is in the freebase form.

In some embodiments, R is hydrogen or hydroxyl. In some embodiments, R is hydrogen. In some embodiments, R is hydroxyl.

In some embodiments, $R_1$, $R_2$ and $R_3$ are each independently selected from hydrogen (H), F, and $C_1$-$C_3$ alkyl. In some embodiments, $R_1$, $R_2$ and $R_3$ are each independently selected from hydrogen (H), F, and methyl. In some embodiments, $R_1$, $R_2$ and $R_5$ are each independently selected from hydrogen (H), F, and $C_1$-$C_3$ alkyl.

In some embodiments, Ri is hydrogen, F, or $C_1$-$C_3$ alkyl. In some embodiments, $R_1$ is hydrogen. In some embodiments, $R_1$ is F. In some embodiments, $R_1$ is $C_1$-$C_3$ alkyl.

In some embodiments, $R_2$ is hydrogen, F, or $C_1$-$C_3$ alkyl. In some embodiments, $R_2$ is hydrogen. In some embodiments, $R_2$ is F. In some embodiments, $R_2$ is $C_1$-$C_3$ alkyl.

In some embodiments, $R_3$ is hydrogen, F, or $C_1$-$C_3$ alkyl. In some embodiments, $R_3$ is hydrogen. In some embodiments, $R_3$ is F. In some embodiments, $R_3$ is $C_1$-$C_3$ alkyl.

In some embodiments, at least one of $R_1$, $R_2$, and $R_3$ are hydrogen. In some embodiments, two of $R_1$, $R_2$, and $R_3$ are hydrogen. In some embodiments, all of $R_1$, $R_2$, and $R_3$ are not hydrogen (e.g., C27 is not —$CH_3$).

In some embodiments, at least one of $R_1$, $R_2$, and $R_3$ are $C_1$-$C_3$ alkyl. In some embodiments, at least one of $R_1$, $R_2$, and $R_5$ are methyl. In some embodiments, at least two of $R_1$, $R_2$, and $R_3$ are $C_1$-$C_3$ alkyl. In some embodiments, at least Formula (I)

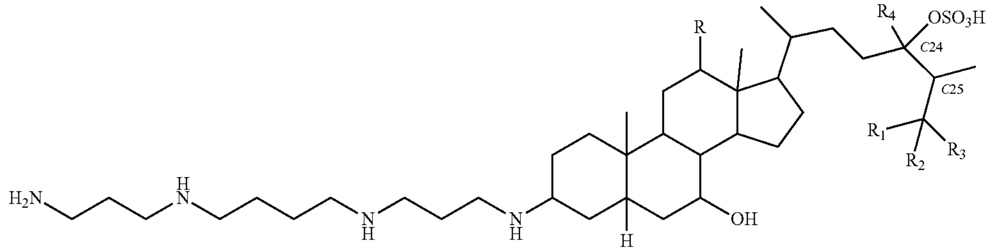

two of $R_1$, $R_2$, and $R_5$ are methyl. In some embodiments, all of $R_1$, $R_2$, and $R_5$ are $C_1$-$C_3$ alkyl. In some embodiments, all of $R_1$, $R_2$, and $R_3$ are methyl.

In some embodiments, $R_1$, $R_2$, and $R_3$ are F.

In some embodiments, $R_1$, $R_2$, and $R_3$ are methyl.

In some embodiments, $R_1$ and $R_2$ are hydrogen and $R_3$ is methyl.

In some embodiments, $R_1$ is hydrogen and $R_2$ and $R_3$ are F.

In some embodiments, $R_1$ is hydrogen, $R_2$ is F, and $R_3$ is methyl.

In some embodiments, $R_4$ is hydrogen or $C_1$-$C_3$ alkyl optionally substituted with hydroxyl. In some embodiments, $R_4$ is hydrogen or $C_1$-$C_3$ alkyl substituted with hydroxyl. In some embodiments, $R_4$ is hydrogen or $CH_2OH$. In some embodiments, $R_4$ is hydrogen. In some embodiments, $R_4$ is $CH_2OH$.

In some embodiments, the stereochemistry of C24 is(S). In some embodiments, the stereochemistry of C24 is (R). In some embodiments, the stereochemistry of C25 is(S). In some embodiments, the stereochemistry of C25 is (R).

In some embodiments, provided herein is a compound of Formula (Ia), or a pharmaceutically acceptable salt, ester, or stereoisomer thereof:

Formula (Ia)

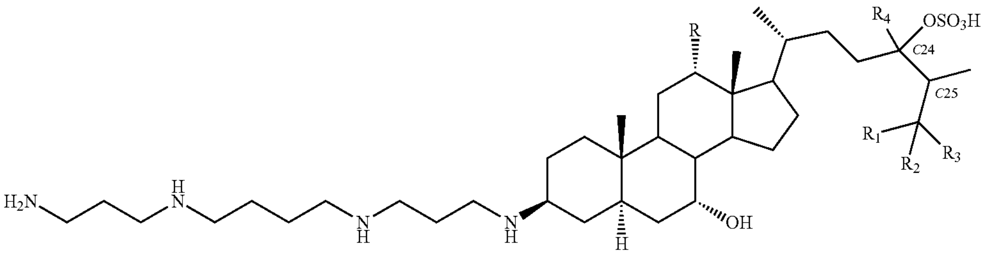

wherein,

R is hydrogen or hydroxyl:

$R_1$, $R_2$ and $R_3$ are each independently selected from hydrogen, F, and $C_1$-$C_3$ alkyl; and $R_4$ is hydrogen or $CH_2OH$.

In some embodiments of Formula (I), at least one of $R_1$, $R_2$ and $R_3$ is, F, or $C_1$-$C_3$ alkyl.

In some embodiments, R is hydrogen or hydroxyl. In some embodiments. R is hydrogen. In some embodiments, R is hydroxyl.

In some embodiments, $R_1$, $R_2$ and $R_5$ are each independently selected from hydrogen (H), F, and $C_1$-$C_3$ alkyl. In some embodiments, $R_1$, $R_2$ and $R_3$ are each independently selected from hydrogen (H), F, and methyl.

In some embodiments, $R_1$ is hydrogen, F, or $C_1$-$C_3$ alkyl. In some embodiments, $R_1$ is hydrogen. In some embodiments, $R_1$ is F. In some embodiments, $R_1$ is $C_1$-$C_3$ alkyl.

In some embodiments, $R_2$ is hydrogen, F, or $C_1$-$C_3$ alkyl. In some embodiments, $R_2$ is hydrogen. In some embodiments, $R_2$ is F. In some embodiments, $R_2$ is $C_1$-$C_3$ alkyl.

In some embodiments, Rs is hydrogen, F, or $C_1$-$C_3$ alkyl. In some embodiments, $R_3$ is hydrogen. In some embodiments, $R_3$ is F. In some embodiments, $R_3$ is $C_1$-$C_3$ alkyl.

In some embodiments, at least one of $R_1$, $R_2$, and $R_5$ are hydrogen. In some embodiments, two of $R_1$, $R_2$, and $R_3$ are hydrogen. In some embodiments, all of $R_1$, $R_2$, and $R_3$ are not hydrogen (e.g., C27 is not —$CH_3$).

In some embodiments, at least one of $R_1$, $R_2$, and $R_5$ are $C_1$-$C_3$ alkyl. In some embodiments, at least one of $R_1$, $R_2$, and $R_5$ are methyl. In some embodiments, at least two of $R_1$, $R_2$, and $R_3$ are $C_1$-$C_3$ alkyl. In some embodiments, at least two of $R_1$, $R_2$, and $R_3$ are methyl. In some embodiments, all of $R_1$, $R_2$, and $R_3$ are $C_1$-$C_3$ alkyl. In some embodiments, all of $R_1$, $R_2$, and $R_3$ are methyl.

In some embodiments, $R_1$, $R_2$, and $R_3$ are F.

In some embodiments, $R_1$, $R_2$, and $R_3$ are methyl.

In some embodiments, $R_1$ and $R_2$ are hydrogen and $R_3$ is methyl.

In some embodiments, $R_1$ is hydrogen and $R_2$ and $R_3$ are F.

In some embodiments, $R_1$ is hydrogen, $R_2$ is F, and $R_3$ is methyl.

In some embodiments, $R_4$ is hydrogen or $C_1$-$C_3$ alkyl optionally substituted with hydroxyl. In some embodiments, $R_4$ is hydrogen or $C_1$-$C_3$ alkyl substituted with hydroxyl. In some embodiments, $R_4$ is hydrogen or $CH_2OH$. In some embodiments, $R_4$ is hydrogen. In some embodiments, $R_4$ is $CH_2OH$.

In some embodiments, the stereochemistry of C24 is(S). In some embodiments, the stereochemistry of C24 is (R). In some embodiments, the stereochemistry of C25 is(S). In some embodiments, the stereochemistry of C25 is (R).

In some embodiments, the compound of Formula (Ia) is of Formula (Ib):

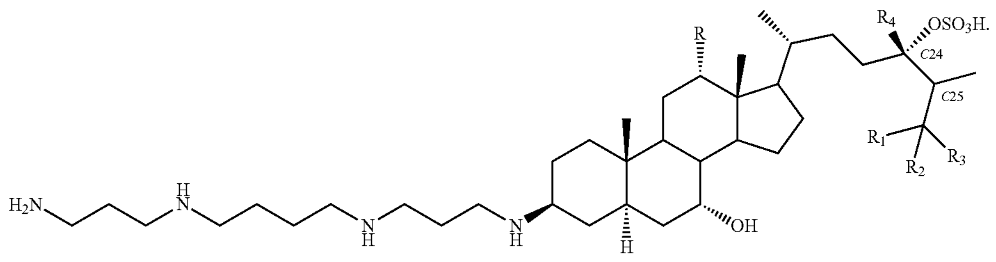

Formula (Ib)

In some embodiments, the compound of Formula (I) is of Formula (Ic):

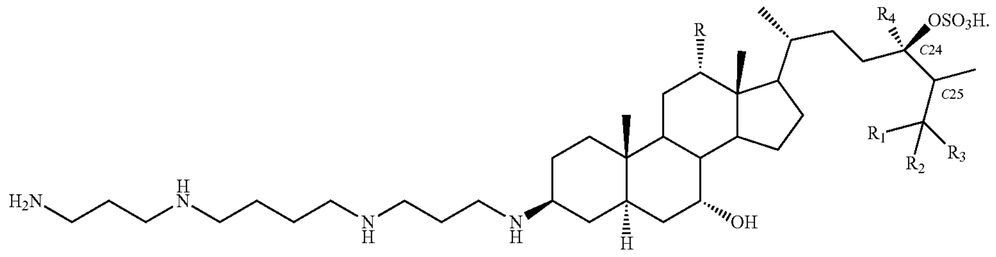

Formula (Ic)

In some embodiments, provided herein is a compound of Formula (II), or a pharmaceutically acceptable salt, ester, or stereoisomer thereof:

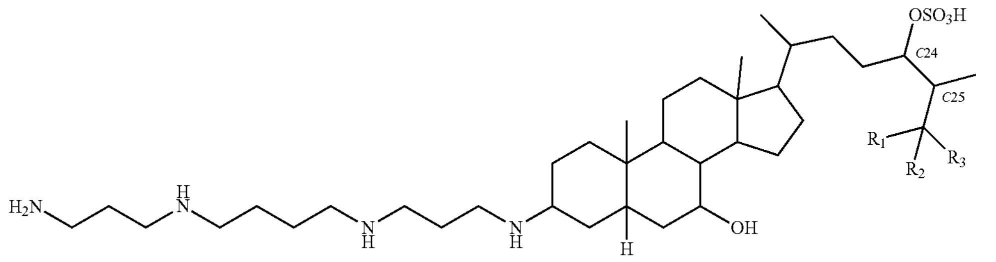

Formula (II)

wherein, $R_1$, $R_2$ and $R_3$ are each independently selected from hydrogen, F, and $C_1$-$C_3$ alkyl, wherein at least one of $R_1$, $R_2$ and $R_3$ is F, or $C_1$-$C_3$ alkyl.

In some embodiments, the compound of Formula (II) is a compound of Formula (IIa), or a pharmaceutically acceptable salt, ester, or stereoisomer thereof:

Formula (IIa)

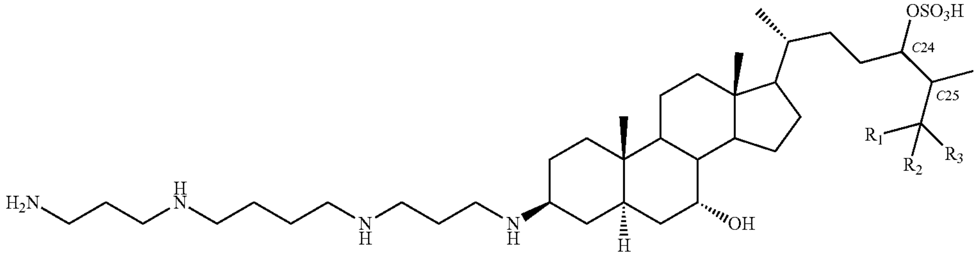

In some embodiments, provided herein is a freebase of the compound of Formula (II). In some embodiments, provided herein is a freebase of the compound of Formula (IIa).

In some embodiments, $R_1$, $R_2$ and $R_5$ are each independently selected from hydrogen (H), F, and $C_1$-$C_3$ alkyl. In some embodiments, $R_1$, $R_2$ and $R_5$ are each independently selected from hydrogen (H), F, and methyl. In some embodiments, $R_1$, $R_2$ and $R_5$ are each independently selected from hydrogen (H), F, and methyl.

In some embodiments, $R_1$ is hydrogen, F, or $C_1$-$C_3$ alkyl. In some embodiments, $R_1$ is hydrogen. In some embodiments, $R_1$ is F. In some embodiments, $R_1$ is $C_1$-$C_3$ alkyl.

In some embodiments, $R_2$ is hydrogen, F, or $C_1$-$C_3$ alkyl. In some embodiments, $R_2$ is hydrogen. In some embodiments, $R_2$ is F. In some embodiments, $R_2$ is $C_1$-$C_3$ alkyl.

In some embodiments, $R_3$ is hydrogen, F, or $C_1$-$C_3$ alkyl. In some embodiments, $R_3$ is hydrogen. In some embodiments, $R_3$ is F. In some embodiments, $R_3$ is $C_1$-$C_3$ alkyl.

In some embodiments, at least one of $R_1$, $R_2$, and $R_3$ are hydrogen. In some embodiments, two of $R_1$, $R_2$, and $R_3$ are hydrogen. In some embodiments, all of $R_1$, $R_2$, and $R_3$ are not hydrogen (e.g., C27 is not —$CH_3$).

In some embodiments, at least one of $R_1$, $R_2$, and $R_3$ are $C_1$-$C_3$ alkyl. In some embodiments, at least one of $R_1$, $R_2$, and $R_5$ are methyl. In some embodiments, at least two of $R_1$, $R_2$, and $R_3$ are $C_1$-$C_3$ alkyl. In some embodiments, at least two of $R_1$, $R_2$, and $R_5$ are methyl. In some embodiments, all of $R_1$, $R_2$, and $R_5$ are $C_1$-$C_3$ alkyl. In some embodiments, all of $R_1$, $R_2$, and $R_3$ are methyl.

In some embodiments, $R_1$, $R_2$, and $R_3$ are F.

In some embodiments, $R_1$, $R_2$, and $R_5$ are methyl.

In some embodiments, $R_1$ and $R_2$ are hydrogen and Rs is methyl.

In some embodiments, $R_1$ is hydrogen and $R_2$ and $R_5$ are F.

In some embodiments, $R_1$ is hydrogen, $R_2$ is F, and $R_3$ is methyl.

In some embodiments, the compound provided herein (e.g., the compound of Formula (I) or (II)) is provided in Table 1.

TABLE 1

| Compound | Structure |
|---|---|
| 1 | 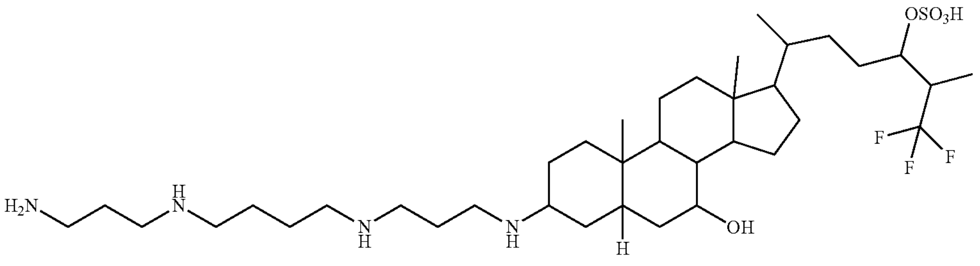 |
| 2 | 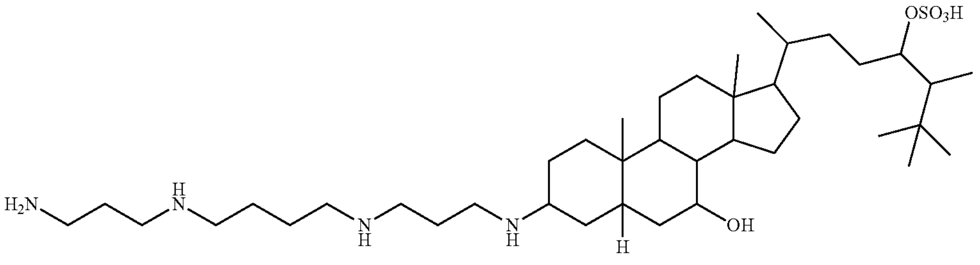 |

TABLE 1-continued
| Compound | Structure |
| --- | --- |
| 3 | 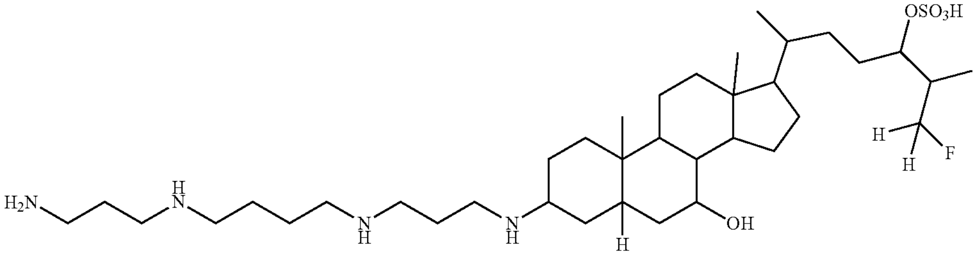 |
| 4 | 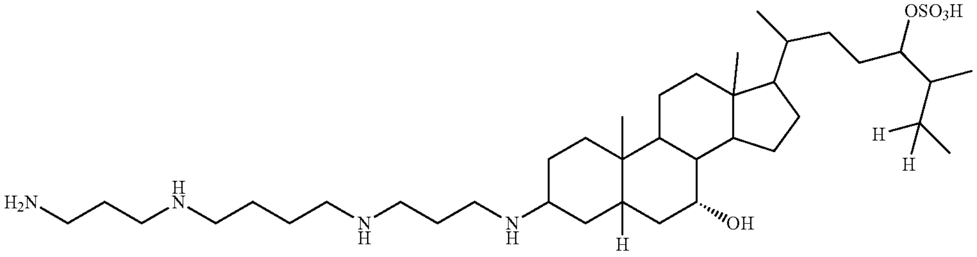 |
| 5 | 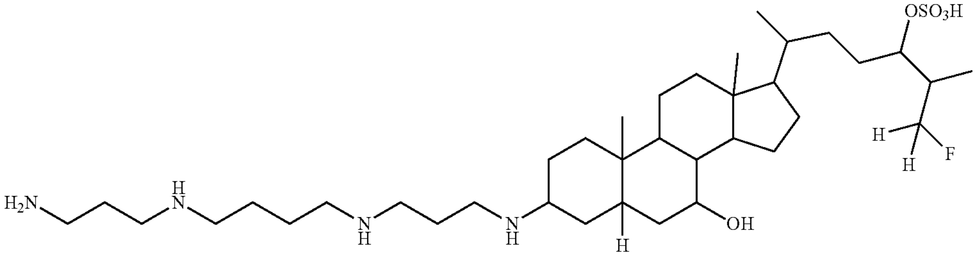 |
| 6 | 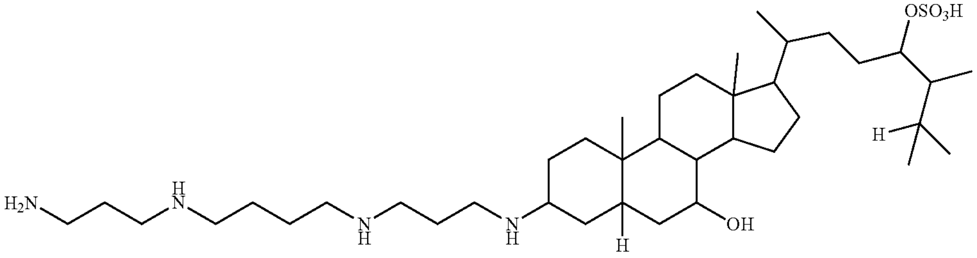 |
In some embodiments, the stereochemistry of C24 is(S) (e.g., C24 is in the(S) orientation). In some embodiments, the compound of Formula (I) is of Formula (IIb), or a pharmaceutically acceptable salt, ester, or stereoisomer thereof:
Formula (IIb)
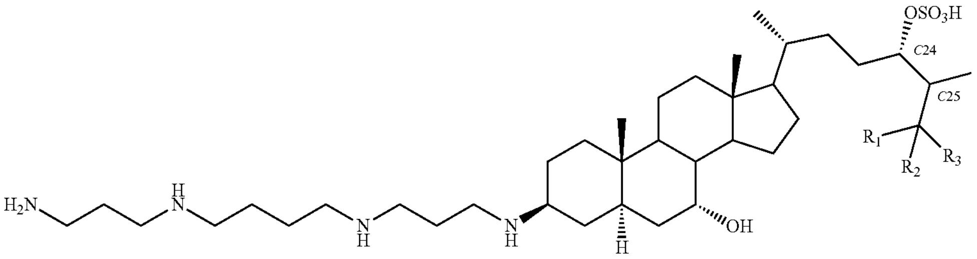

In some embodiments, the compound of Formula (IIb) is a freebase.

In some embodiments, the stereochemistry of C24 is (R) (e.g., C24 is in the (R) orientation). In some embodiments, the compound of Formula (II) is of Formula (IIc), or a pharmaceutically acceptable salt, ester, or stereoisomer thereof:

Formula (IIc)

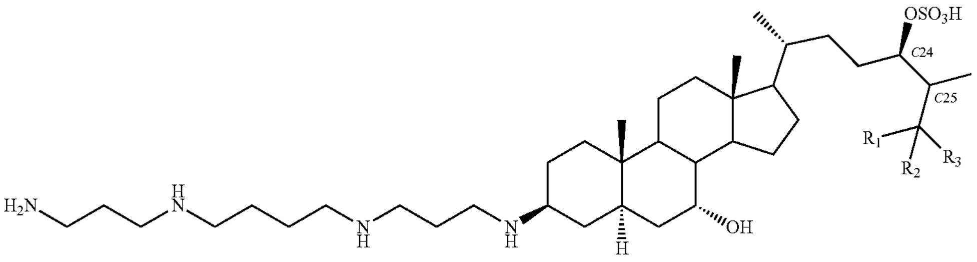

In some embodiments, the compound of Formula (IIc) is a freebase.

In some embodiments, the compound is a compound of Table 2. In some embodiments, the compound of Formula (II), (IIa), (IIb), or (IIc) is selected from a compound in Table 2.

TABLE 2

| Compound | Structure |
|---|---|
| 1a | 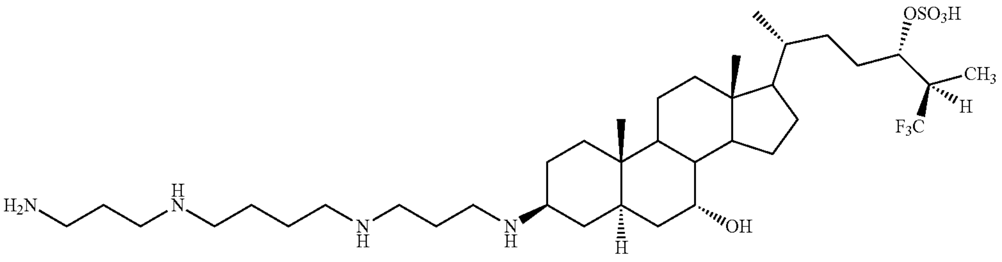 |
| 1b | 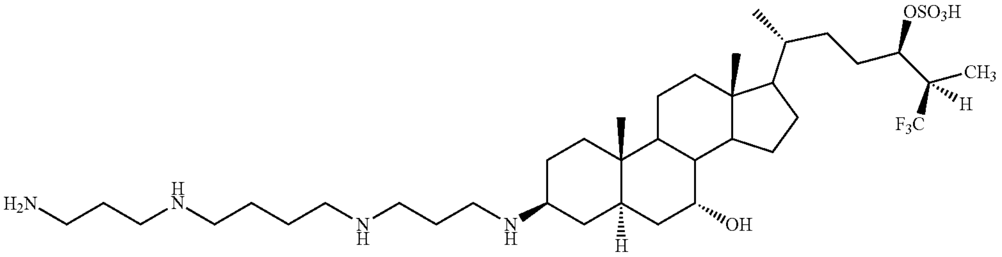 |
| 1c | 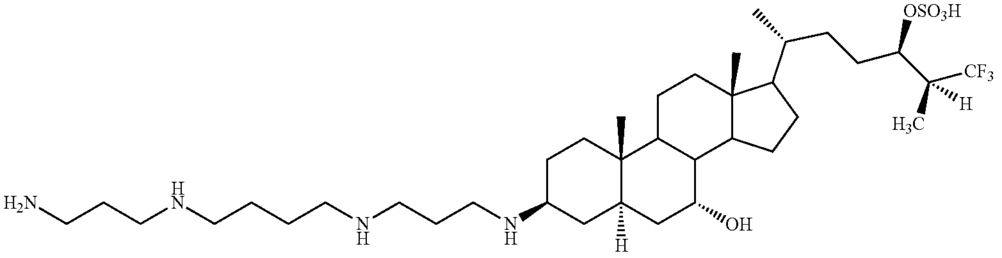 |

TABLE 2-continued

| Compound | Structure |
| --- | --- |
| 1d | 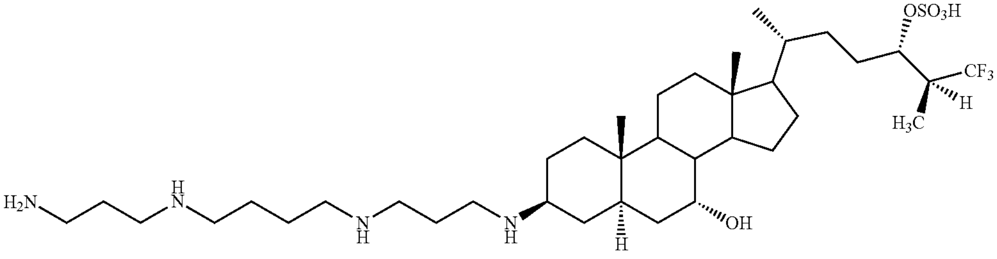 |

In some embodiments, the compound is the freebase form of Compound 1a:

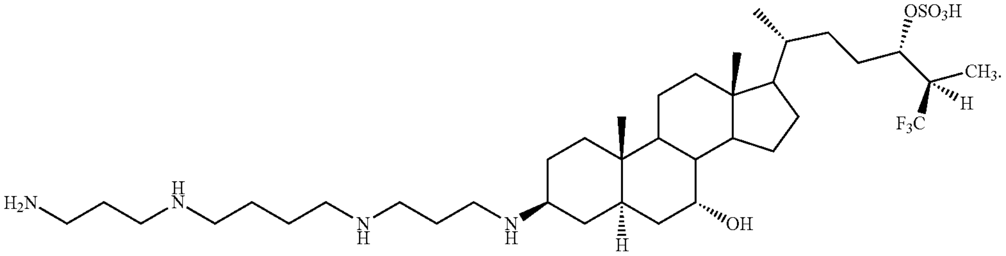

In some embodiments, the compound is a salt of Compound 1a.

In some embodiments, the compound is a free base form of Compound 1b. In some embodiments, the compound is a salt of Compound 1b.

In some embodiments, the compound is a free base form of Compound 1c. In some embodiments, the compound is a salt of Compound 1c.

In some embodiments, the compound is a free base form of Compound 1b. In some embodiments, the compound is a salt of Compound 1d.

In some embodiments, the compound of Formula (I) is of Formula (III):

Formula (III)

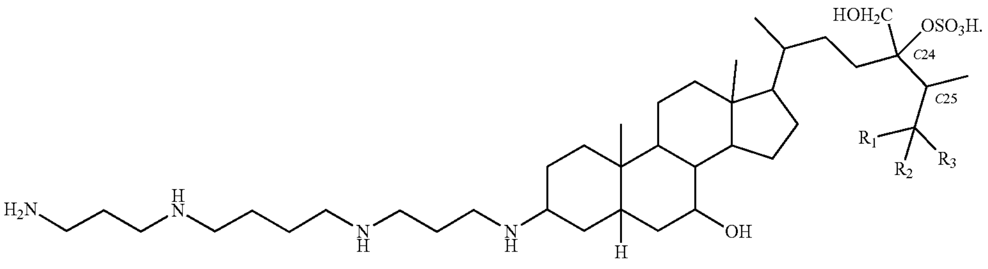

In some embodiments, the compound of Formula (III) is of Formula (IIIa):

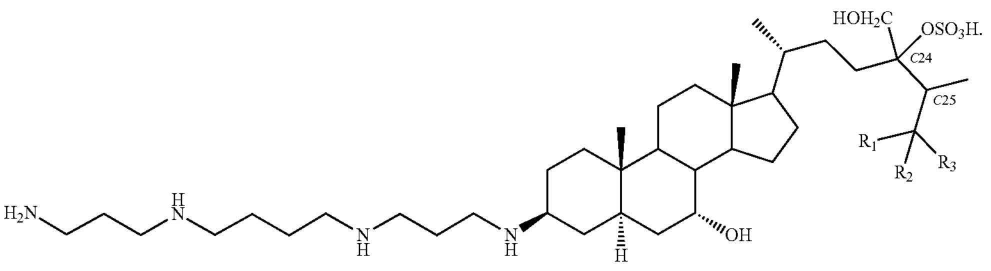

Formula (IIIa)

In some embodiments, the compound of Formula (III) is of Formula (IIIb):

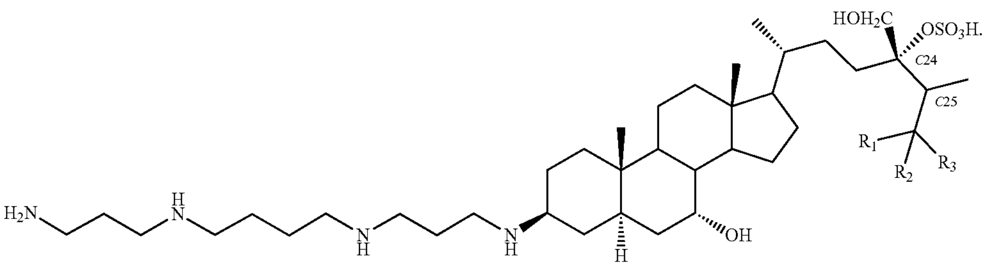

Formula (IIIb)

In some embodiments, the compound of Formula (III) is of Formula (IIIc):

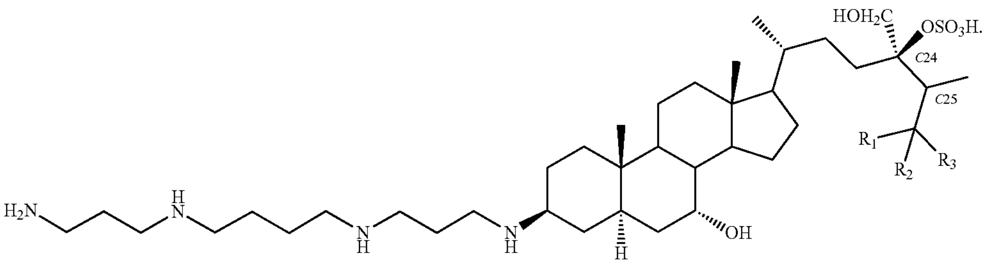

Formula (IIIc)

In some embodiments, $R_1$, $R_2$, and $R_3$ are defined elsewhere herein, and the stereochemistry of each of C24 and C25 can independently be(S) or (R).

In some embodiments, the compound of Formula (I) is of Formula (IV):
Formula (IV)
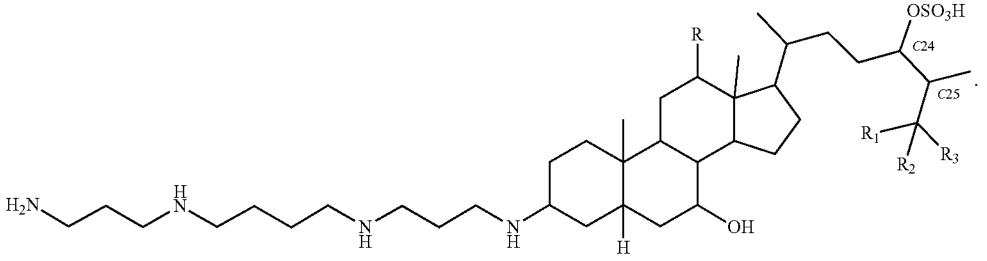
In some embodiments, the compound of Formula (IV) is of Formula (IVa):
Formula (IVa)
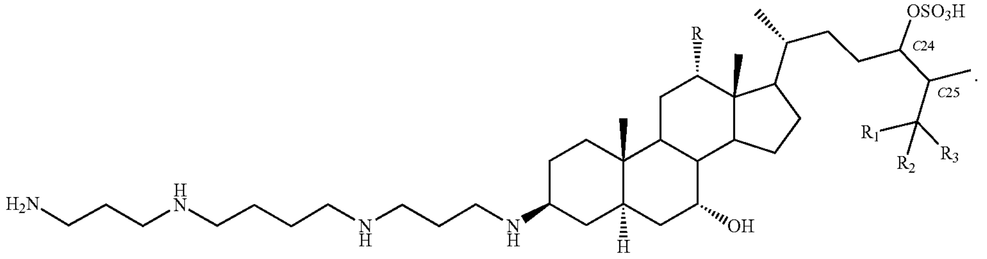
In some embodiments, the compound of Formula (IV) is of Formula (IVb):
Formula (IVb)
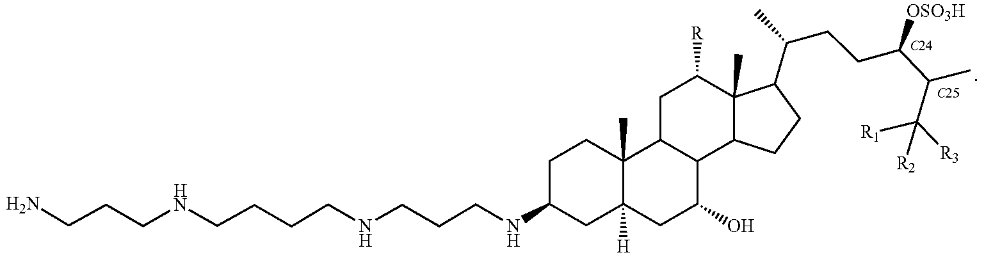
In some embodiments, the compound of Formula (IV) is of Formula (IVc):
Formula (IVc)
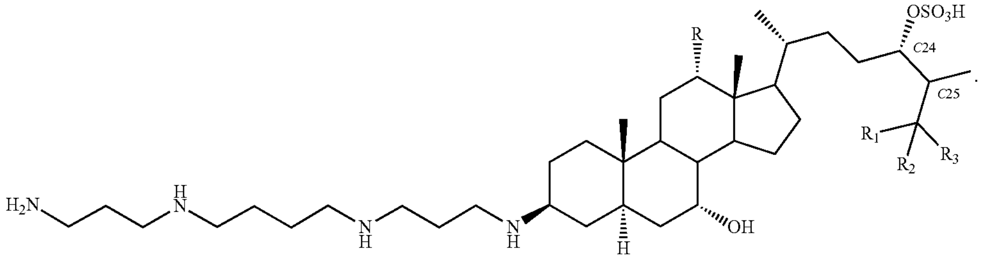

In some embodiments, R, $R_1$, $R_2$, and $R_3$ are defined elsewhere herein, and the stereochemistry of each of C24 and C25 can independently be (S) or (R).

In some embodiments, the compounds provided herein (e.g., the compounds of Formula (I), (II), (III), (IV), or of Table 1, or Table 2) are not racemic. In some embodiments, the compounds provided herein are substantially free of other isomers. In some embodiments, the compounds provided herein comprise 25% or less of other isomers. In some embodiments, the compounds provided herein comprise 20% or less of other isomers. In some embodiments, the compounds provided herein comprise 15% or less of other isomers. In some embodiments, the compounds provided herein comprise 10% or less of other isomers. In some embodiments, the compounds provided herein comprise 5% or less of other isomers. In some embodiments, the compounds provided herein comprise 1% or less of other isomers. In some embodiments, the compounds provided herein comprise 0.5% or less of other isomers.

In some embodiments, the compounds provided herein (e.g., the compounds of Formula (I), (II), (III), (IV), or of Table 1, or Table 2) may be stereochemically pure. In some embodiments, the compounds provided herein have a stereochemical purity of at least 75%. In some embodiments, the compounds provided herein have a stereochemical purity of at least 80%. In some embodiments, the compounds provided herein have a stereochemical purity of at least 85%. In some embodiments, the compounds provided herein have a stereochemical purity of at least 90%. In some embodiments, the compounds provided herein have a stereochemical purity of at least 95%. In some embodiments, the compounds provided herein have a stereochemical purity of at least 96%. In some embodiments, the compounds provided herein have a stereochemical purity of at least 97%. In some embodiments, the compounds provided herein have a stereochemical purity of at least 98%. In some embodiments, the compounds provided herein have a stereochemical purity of at least 99%. In some embodiments, the compounds provided herein have a stereochemical purity of at least 99.5%.

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine, and chloride, such as $^{2}H$ (D), $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts or stereoisomers thereof which contain the aforementioned isotopes and/or other isotopes of other atoms are within the scope of this disclosure. Certain isotopically-labeled compounds, for example those into which radioactive isotopes such as $^{3}H$ and $^{14}C$ are incorporated, are useful in drug and/or substrate tissue distribution assays.

In some embodiments, the compounds described herein are labeled by other means, including, but not limited to, the use of chromophores or fluorescent moieties, bioluminescent labels, or chemiluminescent labels.

In some embodiments, a compound disclosed herein is labeled in the spermine moiety.

In some embodiments, the compounds described herein exist as solvates. In some embodiments, the disclosure provides for methods of treating diseases by administering the compounds in the form of such solvates.

In some embodiments, the compounds provided herein have a (e.g., elimination) half life that is longer than that of the parent (e.g., unmodified) compound. In some embodiments, the compounds provided herein (e.g., Compound 1a) has as half life that is longer than Trodusquemine. In some embodiments, the compounds provided herein have a half life ($T_{1/2}$) of at least 20 hours. In some embodiments, the compounds provided herein have a half life ($T_{1/2}$) of at least 21 hours. In some embodiments, the compounds provided herein have a half life ($T_{1/2}$) of at least 22 hours. In some embodiments, the compounds provided herein have a half life ($T_{1/2}$) of at least 23 hours In some embodiments, the compounds provided herein have a half life ($T_{1/2}$) of about 20 hours, 21 hours. 22 hours. 23 hours, or 24 hours. In some embodiments, the compounds provided herein have a half life ($T_{1/2}$) of from about 20 hours to about 26 hours. In some embodiments, the compounds provided herein have a half life ($T_{1/2}$) of from about 22 hours to about 25 hours. In some embodiments, the compounds provided herein have a half life ($T_{1/2}$) of about 24 hours, such as described in Example 8.

Pharmaceutical Compositions

In some embodiments, provided herein are pharmaceutical compositions comprising one or any combination of the compounds provided herein, or a pharmaceutically acceptable salt, ester, solvate, or stereoisomer thereof.

In some embodiments, a pharmaceutical composition provided herein has a stereochemical purity of at least 75% for the compound disclosed herein. In some embodiments, the pharmaceutical composition has a stereochemical purity of at least 80% for the compound. In some embodiments, the pharmaceutical composition has a stereochemical purity of at least 85% for the compound. In some embodiments, the pharmaceutical composition has a stereochemical purity of at least 90% for the compound. In some embodiments, the pharmaceutical composition has a stereochemical purity of at least 95% for the compound. In some embodiments, the pharmaceutical composition has a stereochemical purity of at least 96% for the compound. In some embodiments, the pharmaceutical composition has a stereochemical purity of at least 97% for the compound. In some embodiments, the pharmaceutical composition has a stereochemical purity of at least 98% for the compound. In some embodiments, the pharmaceutical composition has a stereochemical purity of at least 99% for the compound. In some embodiments, the pharmaceutical composition has a stereochemical purity of at least 99.5% for the compound. In some embodiments, provided herein is a pharmaceutical composition comprising a compound provided herein, such as a compound of Table 1 or Table 2, or a pharmaceutically acceptable salt, ester, or stereoisomer thereof. In some embodiments, provided herein is a pharmaceutical composition comprising a stereochemically pure compound provided herein, such as a compound of Table 1 or Table 2, or a pharmaceutically acceptable salt, ester, or stereoisomer thereof.

In some embodiments, provided herein is a pharmaceutical composition comprising a combination of two or more of the compounds provided herein, such as compounds of Table 1 or Table 2, or a pharmaceutically acceptable salt, ester, or stereoisomer thereof.

In some embodiments, the pharmaceutical compositions provided herein comprise a combination of stereoisomers, such as a combination of isomers provided in Table 2.

In some embodiments, the pharmaceutical composition comprises Compound 1. In some embodiments, the pharmaceutical composition comprises Compound 1a, provided herein. In some embodiments, the pharmaceutical composition comprises Compound 1b, provided herein. In some embodiments, the pharmaceutical composition comprises Compound 1c. In some embodiments, the pharmaceutical composition comprises Compound 1d. In some embodiments, the pharmaceutical composition comprises a mixture of Compounds 1a, 1b, 1c, and 1d.

In some embodiments, the pharmaceutical compositions comprise an active metabolite of a compound provided herein.

In some instances, the pharmaceutical compositions comprise at least one pharmaceutically acceptable excipient (e.g. one or more than one pharmaceutically acceptable excipient).

In some embodiments, the pharmaceutically acceptable excipient includes, but is not limited to, a binder, filler, diluent, disintegrant, wetting agent, lubricant, glidant, coloring agent, dye migration inhibitor, sweetening agent, flavoring agent, or a combination thereof.

In some embodiments, the pharmaceutical composition comprises a carrier. In some embodiments, the carrier is water. In some embodiments, the carrier comprise saline solution.

In some embodiments, the pharmaceutical composition comprises a binder. Binders or granulators may impart cohesiveness to a tablet to ensure the tablet remains intact after compression. Binders or granulators may include, but are not limited to, starches; gelatin; sugars; natural and synthetic gums; celluloses; microcrystalline celluloses; and mixtures thereof.

In some embodiments, the pharmaceutical composition comprises a filler. Fillers may include, but are not limited to, talc, calcium carbonate, microcrystalline cellulose, powdered cellulose, dextrates, kaolin, mannitol, silicic acid, sorbitol, starch, pre-gelatinized starch, and mixtures thereof.

In some embodiments, the pharmaceutical composition comprises a diluent. Diluents may include, but are not limited to, dicalcium phosphate, calcium sulfate, lactose, sorbitol, sucrose. inositol, cellulose, kaolin, mannitol, sodium chloride, dry starch, and powdered sugar. Certain diluents, such as mannitol, lactose, sorbitol, sucrose, and inositol, when present in sufficient quantity, may impart properties to some compressed tablets that permit disintegration in the mouth by chewing. Such compressed tablets may be used as chewable tablets. In some embodiments, the diluent is lactose monohydrate.

In some embodiments, the pharmaceutical composition comprises a disintegrant. Disintegrants may include, but are not limited to, agar; bentonite; celluloses; wood products; natural sponge; cation-exchange resins; alginic acid; gums, such as guar gum and Veegum HV; citrus pulp; cross-linked celluloses; cross-linked polymers; cross-linked starches; calcium carbonate; microcrystalline cellulose; polacrilin potassium; starches; clays; aligns; and mixtures thereof. The amount of disintegrant in the compositions described herein may vary.

In some embodiments, the pharmaceutical composition comprises a lubricant. Lubricants may include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil; zinc stearate; ethyl oleate; ethyl laureate; agar; starch; lycopodium; silica or silica gels; and mixtures thereof.

In some embodiments, the pharmaceutical composition comprises a glidant. Glidants may be colloidal silicon dioxide. CAB-O-SILR (Cabot Co. of Boston, MA), and talc, including asbestos-free talc.

In some embodiments, the pharmaceutical composition comprises a coloring agent. Coloring agents may include any one of the approved, certified, water soluble FD&C dyes, and water insoluble FD&C dyes suspended on alumina hydrate, and color lakes and mixtures thereof.

In some embodiments, the pharmaceutical composition comprises a flavoring agent. Flavoring agents may include, but are not limited to natural flavors extracted from plants, such as fruits, and synthetic blends of compounds that provide a pleasant taste sensation, such as peppermint and methyl salicylate. In some embodiments, the pharmaceutical composition comprises a sweetening agent. Sweetening agents may include sucrose, lactose, mannitol, syrups, glycerin, sucralose, and artificial sweeteners, such as saccharin, stevioside (*Stevia*) and aspartame.

In some embodiments, the pharmaceutical compositions comprise an emulsifying agent. Emulsifying agents may include, but are not limited to gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate.

In some embodiments, the pharmaceutical compositions comprise suspending and dispersing agents. Suspending and dispersing agents may include sodium carboxymethylcellulose. pectin, tragacanth. Veegum, acacia, sodium carbomethylcellulose, hydroxypropyl methylcellulose (HPMC), and polyvinylpyrolidone.

In some embodiments, the pharmaceutical composition comprises hydroxypropyl methylcellulose (HPMC). In some embodiments, the pharmaceutical composition comprises HPMC in an amount of at least about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, or about 1 wt %. In some embodiments, the pharmaceutical composition comprises HPMC in an amount of at most about 1 wt %, about 0.9 wt %, about 0.8 wt %, about 0.7 wt %, about 0.6 wt %, about 0.5 wt %, about 0.4 wt %, about 0.3 wt %, about 0.2 wt %, or about 0.1 wt %. In some embodiments, the pharmaceutical composition comprises HPMC in an amount of about 0.1 wt % to about 1 wt %, about 0.2 wt % to about 0.9 wt %, about 0.2 wt % to about 0.6 wt %, about 0.3 wt % to about 0.5 wt %, about 0.4 wt % to about 0.8 wt %, or about 0.4 wt % to about 0.6 wt %. In some embodiments, the pharmaceutical composition comprises HPMC in an amount of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, or about 1 wt %. In some embodiments, the pharmaceutical composition comprises HPMC in an amount of about 0.4 wt %.

In some embodiments, the pharmaceutical compositions comprise a preservative. Preservatives may include glycerin, methyl and propylparaben, benzoic add, sodium benzoate and alcohol.

In some embodiments, the pharmaceutical compositions comprise a wetting agent. Wetting agents may include propylene glycol monostearate, sorbitan monooleate, diethylene glycol monolaurate, and polyoxyethylene lauryl ether.

In some embodiments, the pharmaceutical compositions comprise a solvent. Solvents may include but are not limited to glycerin, sorbitol, ethyl alcohol, and syrup.

Examples of non-aqueous liquids utilized in emulsions may include mineral oil and cottonseed oil. Organic acids include but are not limited to citric and tartaric acid.

The pharmaceutical compositions provided herein may be formulated for administration by a variety of means including orally, intranasally, parenterally, by inhalation spray, topically, or rectally in formulations containing pharmaceutically acceptable carriers, adjuvants and vehicles. The term "parenteral" as used here includes subcutaneous, intravenous, intramuscular, intrathecal and intraarterial injections with a variety of infusion techniques. Intraarterial, intrathecal and intravenous injection as used herein may include administration through catheters.

The pharmaceutical compositions provided herein may be formulated in accordance with the routine procedures adapted for desired administration route. Accordingly, the pharmaceutical compositions described herein can take such forms as suspensions, solutions or emulsions in oily or aqueous vehicles, and can contain formulatory agents such as suspending, stabilizing and/or dispersing agents. The compositions described herein may be formulated as a preparation for implantation or injection. Thus, for example, the pharmaceutical compositions described herein can be formulated with polymeric or hydrophobic materials (e.g., as an emulsion in an acceptable oil) or ion exchange resins, or as sparingly soluble derivatives (e.g., as a sparingly soluble salt). The compounds described herein, and the pharmaceutical compositions described herein can be in powder form for constitution with a vehicle, e.g., sterile pyrogen-free water, before use. Formulations for each of these methods of administration can be found, for example, in Remington: The Science and Practice of Pharmacy. A. Gennaro, ed., 20th edition. Lippincott. Williams & Wilkins. Philadelphia, PA.

In some embodiments, the pharmaceutical compositions described herein are formulated for oral administration. These pharmaceutical compositions may comprise solid, semisolid, gelmatrix or liquid dosage forms. As used herein, oral administration may include buccal, lingual, and sublingual administration. The pharmaceutical compositions described herein can be formulated for oral administration in the form of a tablet or a capsule. In some embodiments, the pharmaceutical composition is a liquid formulation. In some embodiments, the pharmaceutical composition is a subcutaneous formulation.

In some embodiments, the pharmaceutical compositions described herein are formulated for intranasal administration. These pharmaceutical compositions may comprise solid or liquid dosage forms. The pharmaceutical compositions described herein may be formulated for intranasal administration in the form of aerosol, nasal spray, etc. The formulation for intranasal administration may be water-based, hydroalcoholic, nonaqueous, suspension, or emulsions. The formulation may comprise pharmaceutically acceptable excipients, including solvents, mucoadhesive agents, buffers, antioxidants, preservatives, and penetration enhancers (i.e., compounds to improve absorption or penetration).

In some embodiments, the pharmaceutical compositions provided herein comprise from about 1 mg to about 5000 mg of a compound provided herein or any amount ranging from and to these values. In some embodiments, the pharmaceutical compositions provided herein comprise from about 1 mg to about 4000 mg of a compound provided herein or any amount ranging from and to these values. In some embodiments, the pharmaceutical compositions provided herein comprise from about 1 mg to about 3000 mg of a compound provided herein or any amount ranging from and to these values. In some embodiments, the pharmaceutical compositions provided herein comprise from about 1 mg to about 2000 mg of a compound provided herein or any amount ranging from and to these values. In some embodiments, the pharmaceutical compositions provided herein comprise from about 1 mg to about 1000 mg of a compound provided herein or any amount ranging from and to these values. In some embodiments, the compositions provided herein comprise from about 1 mg to about 500 mg of a compound provided herein or any amount ranging from and to these values. In some embodiments, the compositions provided herein comprise from about 1 mg to about 400 mg of a compound provided herein or any amount ranging from and to these values. In some embodiments, the compositions provided herein comprise from about 1 mg to about 200 mg of a compound provided herein or any amount ranging from and to these values. In some embodiments, the pharmaceutical compositions provided herein comprise from about 1 mg to about 100 mg of a compound provided herein or any amount ranging from and to these values.

In some embodiments, the pharmaceutical compositions comprise the compound in an amount of at least 0.1 mg/mL. In some embodiments, the pharmaceutical compositions comprise the compound in an amount of at least 0.2 mg/mL, 0.3 mg/mL, 0.5 mg/mL, 1 mg/mL, 2 mg/mL. 4 mg/mL, 5 mg/mL, 6 mg/mL, 8 mg/mL, or at least 10 mg/mL. In some embodiments, the pharmaceutical compositions comprise the compound in an amount of at most 15 mg/mL, 12 mg/mL, 10 mg/mL, 8 mg/mL, 6 mg/mL, 5 mg/mL, 4 mg/mL, 2 mg/mL, or at most 1 mg/mL. In some embodiments, the pharmaceutical compositions comprise the compound in an amount of at least 5 mg/mL. In some embodiments, the pharmaceutical compositions comprise the compound in an amount of at least 10 mg/mL. In some embodiments, the pharmaceutical compositions comprise the compound in an amount of at least 20 mg/mL. In some embodiments, the pharmaceutical compositions comprise the compound in an amount of at least 30 mg/mL. In some embodiments, the pharmaceutical compositions comprise the compound in an amount of at most 70 mg/mL. In some embodiments, the pharmaceutical compositions comprise the compound in an amount of at most 60 mg/mL. In some embodiments, the pharmaceutical compositions comprise the compound in an amount of at most 50 mg/mL. In some embodiments, the pharmaceutical compositions comprise the compound in an amount of at most 40 mg/mL. In some embodiments, the pharmaceutical compositions comprise the compound in an amount of from about 1 mg/mL to about 50 mg/mL. In some embodiments, the pharmaceutical compositions comprise the compound in an amount of from about 0.1 mg/mL to about 15 mg/mL, about 0.1 mg/mL to about 10 mg/mL, about 0.1 mg/mL to about 1 mg/mL or about 5 mg/mL to about 15 mg/mL. In some embodiments, the pharmaceutical composition comprises the compound in an amount of from about 0.2 mg/mL to about 0.8 mg/mL. In some embodiments, the pharmaceutical composition comprises the compound in an amount of about 0.5 mg/mL. In some embodiments, the pharmaceutical composition comprises the compound in an amount of 8 mg/mL to about 11 mg/mL. In some embodiments, the pharmaceutical composition comprises the compound in an amount of about 10 mg/mL. In some embodiments, the pharmaceutical composition comprises the compound in an amount of about 5 mg/mL. In some embodiments, the pharmaceutical composition comprises the compound in an amount of about 0.5 mg/mL.

In some embodiments, the pharmaceutical compositions described herein comprise a compound provided herein in an amount of about 10 wt % to about 99 wt % of the total weight of the pharmaceutical composition provided herein. In some embodiments, the pharmaceutical compositions described herein comprise a compound provided herein in an amount of about 1 wt % to about 10 wt % of the total weight of the pharmaceutical composition provided herein.

In some embodiments, the pharmaceutical compositions comprise a solubilizing agent. In some embodiments, the pharmaceutical compositions comprise a solubilizing agent. In some embodiments, the pharmaceutical compositions comprise a solubilizing agent in an amount of at least 1 wt %. 2 wt %. 4 wt %. 5 wt %. 6 wt %. 8 wt %, or 10 wt %. In some embodiments, the pharmaceutical compositions comprise a solubilizing agent in an amount of at most 15 wt %. 14 wt %. 13 wt %. 12 wt %. 11 wt %, or 10 wt %. In some embodiments, the pharmaceutical compositions comprise a solubilizing agent in an amount of from about 1 wt % to about 15 wt %, from about 5 wt % to about 15 wt %, from about 8 wt % to about 15 wt %, or from about 9 wt % to about 12 wt %. In some embodiments, the pharmaceutical compositions comprise a solubilizing agent in an amount of from about 9 wt % to about 11 wt %. In some embodiments, the pharmaceutical compositions comprise a solubilizing agent in an amount of about 10 wt %. In some embodiments, the solubilizing agent is β-cyclodextrin. In some embodiments, the solubilizing agent is 2-hydroxypropyl β-cyclodextrin. In some embodiments, the solubilizing agent is β-cyclodextrin sulfobutyl ether sodium salt (SBEbCD).

In some embodiments, the pharmaceutical compositions comprise a solubilizing agent in an amount of at least about 20 mg/mL, about 40 mg/mL, about 60 mg/mL, about 80 mg/mL, about 100 mg/mL, about 120 mg/mL, about 140 mg/mL, about 160 mg/mL, about 180 mg/mL, or about 200 mg/mL. In some embodiments, the pharmaceutical compositions comprise a solubilizing agent in an amount of at most about 250 mg/mL, 230 mg/mL, 200 mg/mL, about 180 mg/mL, about 160 mg/mL, about 140 mg/mL, about 120 mg/mL, about 100 mg/mL, about 80 mg/mL, about 60 mg/mL, about 40 mg/mL, or about 20 mg/mL. In some embodiments, the pharmaceutical compositions comprise a solubilizing agent in an amount of about 20 mg/mL to about 200 mg/mL, about 40 mg/mL to about 180 mg/mL, about 60 mg/mL to about 140 mg/mL, about 80 mg/mL to about 120 mg/mL, about 100 mg/mL to about 180 mg/mL, or about 100 mg/mL to about 140 mg/mL. In some embodiments, the pharmaceutical compositions comprise a solubilizing agent in an amount of about 20 mg/mL, about 40 mg/mL, about 60 mg/mL, about 80 mg/mL, about 100 mg/mL, about 120 mg/mL, about 140 mg/mL, about 160 mg/mL, about 180 mg/mL, about 200 mg/mL, or about 250 mg/mL. In some embodiments, the pharmaceutical compositions comprise a solubilizing agent in an amount of from about 80 mg/mL to about 120 mg/mL. In some embodiments, the pharmaceutical compositions comprise a solubilizing agent in an amount of about 100 mg/mL. In some embodiments, the pharmaceutical compositions comprise a solubilizing agent in an amount of about 2 to 25 wt % of the composition. In some embodiments, the pharmaceutical compositions comprise a solubilizing agent in an amount of about 5 to 15 wt % of the composition. In some embodiments, the pharmaceutical compositions comprise a solubilizing agent in an amount of about 8 to 12 wt % of the composition. In some embodiments, the pharmaceutical compositions comprise a solubilizing agent in an amount of about 10 wt % of the composition. In some embodiments, the solubilizing agent is 2-hydroxypropyl β-cyclodextrin.

In some embodiments, the pharmaceutical compositions comprise a buffering agent, some embodiments, the pharmaceutical composition comprises the buffering agent in a concentration of at least 1 mM, 5 mM, 10 mM, 15 mM, 20 mM, 25 mM, 30 mM, 40 mM, 50 mM, or 60 mM. In some embodiments, the pharmaceutical composition comprises the buffering agent in a concentration of at most 100 mM, 50 mM, 45 mM, 40 mM, 35 mM, 30 mM, or 25 mM. In some embodiments, the pharmaceutical composition comprises the buffering agent in a concentration of from about 1 mM to about 50 mM, 5 mM to about 45 mM, 10 mM to about 40 mM, 20 mM to about 35 mM, or 25 mM to about 35 mM. In some embodiments, the pharmaceutical composition comprises the buffering agent in a concentration of about 30 mM. In some embodiments, the pharmaceutical composition comprises the buffering agent in a concentration of from about 20 mM to about 80 mM. In some embodiments, the buffering agent is $NaHCO_3$. In some embodiments, the buffering agent is a phosphate buffer.

In some embodiments, the pH of the pharmaceutical composition is about 7.4. In some embodiments, the pH of the pharmaceutical composition is 5-8. In some embodiments, the pH of the pharmaceutical composition is 7-8. In some embodiments, the pH of the pharmaceutical composition is 7-7.5. In some embodiments, the pH of the pharmaceutical composition is 6-8.

In some embodiments, the pharmaceutical composition comprises a tonicity agent. In some embodiments, the pharmaceutical composition comprises A tonicity agent in a concentration of at least about 90 mM, about 95 mM, about 100 mM, about 105 mM, about 110 mM, about 115 mM, about 120 mM, about 125 mM, about 130 mM, or about 140 mM. In some embodiments, the pharmaceutical composition comprises A tonicity agent in a concentration of at most about 140 mM, about 130 mM, about 125 mM, about 120 mM, about 115 mM, about 110 mM, about 105 mM, about 100 mM, about 95 mM, or about 90 mM. In some embodiments, the pharmaceutical composition comprises A tonicity agent in a concentration of about 90 mM to about 140 mM, about 95 mM to about 130 mM, about 110 mM to about 130 mM, about 115 mM to about 125 mM, about 100 mM to about 120 mM, or about 110 mM to about 120 mM. In some embodiments, the pharmaceutical composition comprises A tonicity agent in a concentration of about 90 mM, about 95 mM, about 100 mM, about 105 mM, about 110 mM, about 115 mM, about 120 mM, about 125 mM, about 130 mM, or about 140 mM. In some embodiments, the pharmaceutical composition comprises A tonicity agent in a concentration of about 120 mM. In some embodiments, the tonicity agent is NaCl or KCl. In some embodiments, the tonicity agent is NaCl.

In some embodiments, the (e.g., subcutaneous) pharmaceutical composition comprises (such as described in Example 3):

(a) from about 5 mg/mL to about 50 mg/mL of a compound provided herein (e.g., Compound 1a);

(b) from about 20 mM to about 80 mM phosphate buffer (about pH 6-8); and (c) from about 80 mg/mL to about 250 mg/mL 2-hydroxypropyl β-cyclodextrin in water.

In some embodiments, the (e.g., subcutaneous) pharmaceutical composition comprises (such as described in Example 3):

(a) about 10 mg/mL of a compound provided herein (e.g., Compound 1a);

(b) about 30 mM phosphate buffer (about pH 7.4); and (c) about 100 mg/mL 2-hydroxypropyl β-cyclodextrin in water.

In some embodiment, the (e.g., intranasal) pharmaceutical composition comprises:

(a) from about 0.2 mg/mL to about 0.6 mg/mL of a compound provided herein (e.g., Compound 1a);

(b) from about 110 mM to about 130 mM NaCl;

(c) from about 10 mM to about 30 mM $NaHCO_3$;

(d) and from about 0.2 wt % to about 0.5 wt % hydroxypropyl methylcellulose.

In some embodiment, the (e.g., intranasal) pharmaceutical composition comprises:

(a) about 0.5 mg/mL of a compound provided herein (e.g., Compound 1a);

(b) about 120 mM NaCl;

(c) about 20 mM $NaHCO_3$;

(d) and about 0.4 wt % hydroxypropyl methylcellulose.

Methods of Treatment

Provided herein are methods of treating a disease in a subject in need thereof comprising administering to the subject a therapeutically effective amount of any of the compounds provided herein (e.g., a compound of Table 1 or Table 2, such as Compound 1a). In some embodiments, provided herein are methods of treating a disease in a subject in need thereof comprising administering to the subject a therapeutically effective amount of a pharmaceutical composition provided herein.

In some embodiments, provided herein are methods of treating or preventing a disease in a subject in need thereof. In some embodiments, the method comprises administering to the subject a therapeutically effective amount of a compound provided herein (e.g., a compound of Table 1 or Table 2, such as Compound 1a). In some embodiments, the method comprises administering to the subject a therapeutically effective amount of a pharmaceutical composition provided herein.

In some embodiments, provided herein are methods of treating or ameliorating the symptoms of a disease in a subject in need thereof. In some embodiments, the method comprises administering to the subject a therapeutically effective amount of a compound provided herein (e.g., a compound of Table 1 or Table 2, such as Compound 1a). In some embodiments, the method comprises administering to the subject a therapeutically effective amount of a pharmaceutical composition provided herein.

In some embodiments, provided herein are methods of slowing the progress of a disease in a subject in need thereof. In some embodiments, the method comprises administering to the subject a therapeutically effective amount of a compound provided herein (e.g., a compound of Table 1 or Table 2, such as Compound 1a). In some embodiments, the method comprises administering to the subject a therapeutically effective amount of a pharmaceutical composition provided herein.

In some embodiments, the method comprises (e.g., optionally) using a dosing regimen.

In some embodiments, the compounds or pharmaceutical compositions provided herein are administered according to a dosing regimen comprising hourly, daily, weekly, or monthly administration. For instance, the compounds or pharmaceutical compositions may be administered three times a day, twice a day, once a day, once a week, or once a month. In some embodiments, the compounds or pharmaceutical compositions provided herein may be administered without food. In some embodiments, the compounds or pharmaceutical compositions provided herein may be administered with food. In some embodiments, the appropriate length of treatment, dosages, and route of administration may be determined and/or adjusted by a physician. In some embodiments, the compounds or pharmaceutical compositions provided herein are administered in a dose escalation scheme. In some embodiments, the compounds or pharmaceutical compositions provided herein are administered every 2-12 weeks. In some embodiments, the compounds or pharmaceutical compositions provided herein are administered every 2-6 weeks. In some embodiments, the compounds or pharmaceutical compositions provided herein are administered every 3 weeks. In some embodiments, the compounds or pharmaceutical compositions provided herein are administered every 4 weeks. In some embodiments, the compounds or pharmaceutical compositions provided herein are administered every 5 weeks. In some embodiments, the compounds or pharmaceutical compositions provided herein are administered every 6 weeks. In some embodiments, the compounds or pharmaceutical compositions provided herein are administered subcutaneously or via IV.

In some embodiments, a subcutaneous dosing regimen comprises administration of a liquid pharmaceutical composition provided herein (e.g., 1 mL), optionally followed by reduction in dosing frequency using metabolic parameters as a determinant.

In some embodiments, an intranasal dosing regimen comprises one to two sprays per nostril (e.g., each spray delivering about 0.1 mL of a pharmaceutical composition provided herein), once, twice, or three times daily at the start of treatment, optionally followed by reduction in dosing frequency using metabolic parameters as a determinant.

In some embodiments, the method comprises (e.g., optionally) monitoring the effect of the treatment using symptoms and/or biomarkers. The biomarkers may be metabolic biomarkers.

In some embodiments, the effect of treatment, prevention, amelioration of the disease or symptoms thereof and/or slowing the progress of disease upon administration of a compound or pharmaceutical composition provided herein can be monitored by measurement of levels of biomarkers in body fluids such as blood, plasma, cerebrospinal fluid (CSF), etc.

In some embodiments, administration of a compound or pharmaceutical composition provided herein improves insulin sensitivity in subjects. In some embodiments, body weight, blood glucose. HbA1c, insulin or trigylcerides can serve to monitor the pharmacodynamics of the compounds provided herein. For instance, the initial daily dosing schedule may be reduced to less frequent dosing once fasting blood glucose has reached normoglycemia or weight reduction is observed. In some embodiments, blood markers associated with aging can be followed, including, but not exclusively restricted to inflammatory cytokines. C-reactive protein, cytotoxic and memory CD8 T cells, and regulatory CD4 T cells.

In some embodiments, the dosing regimen is determined and/or adjusted on the basis of at least one metabolic parameter selected from body weight, blood glucose, blood HBA1c, and/or insulin. In some embodiments, the dosing regimen is determined and/or adjusted on the basis of body weight. In some embodiments, the dosing regimen is determined and/or adjusted on the basis of blood glucose. In some embodiments, the dosing regimen is determined and/or adjusted on the basis of blood HBA1c. In some embodiments, the dosing regimen is determined and/or adjusted on the basis of insulin. In some embodiments, the dosing regimen is determined and/or adjusted on the basis of trigylcerides.

In some embodiments, the disease is an age-related disease. In some embodiments, the age-related disease is an age-related neurodegenerative disease.

In some embodiments, the disease is a metabolic disease or disorder. In some embodiments, the disease is a metabolic disease. In some embodiments, the disease is a metabolic disorder. In some embodiments, the metabolic disease or disorder is equine metabolic syndrome. In some embodiments, the metabolic disease or disorder is equine laminitis. In some embodiments, the metabolic disease or disorder is obesity (e.g., in a dog or in a horse). In some embodiments, the disease is cancer.

The methods provided herein may comprise administration of the compound or pharmaceutical composition by any suitable route of administration including oral, intravenous, subcutaneous, topical, intraperitoneal, intramuscular, transdermal, intranasal, intrathecal, and intralumbar. In some embodiments, the compound or pharmaceutical composition is administered subcutaneously or intranasally. In some embodiments, a therapeutically effective amount of the compound provided herein may be between 0) and 1.000 mg/kg.

In some embodiments, the subject is a mammal. In some embodiments, the subject is a human. In some embodiments, the subject is a non-human mammal. In some embodiments, the subject is a cat, dog, horse, or pony. The subject may be a non-human mammal (e.g., for treatment of metabolic syndrome or pituitary pars intermedia dysfunction in horses). In some embodiments, the subject is a cat. In some embodiments, the subject is a dog. In some embodiments, the subject is a horse. In some embodiments, the subject is an Arabian horse. In some embodiments, the subject is a mustang. In some embodiments, the horse is selected from Saddlebred, Tennessee Walking Horse, Paso Fino, Morgan, Mustang, and Quarter horse breeds. In some embodiments, the subject is a pony. In some embodiments, the horse is 5 to 16 years of age. In some embodiments, the horse is at least 2, 3, 4, or 5 years of age. In some embodiments, the horse is at most 10, 11, 12, 13, 14, 15, 16, 17, 18, 19, or 20 years of age. In some embodiments, the horse is 15 years of age or younger. In some embodiments, the subject is a donkey. In some embodiments, the subject (such as a horse) is overweight. In some embodiments, the subject (such as a horse) is obese.

The subject may be a "pet" comprising a cat, dog, horse, or pony.

In the methods described herein, a compound provided herein can be as reference compound, for example to assess one or more biological activities of another compound (e.g., an enantiomer of the reference compound) or to improve a structure-activity relationship algorithm.

Compounds provided herein and the pharmaceutical compositions described herein can be used as inhibitors or activators in preclinical models to study metabolic routes or screen other compounds. For instance, identification of redundant pathways can be identified after administration of compounds provided herein.

Compounds provided herein and the compositions described herein can be used as diagnostic agents. For example, compounds and compositions can be used for molecular imaging when a radionuclide is included in their structure (e.g., $^{18}F$).

The compounds provided herein, and the pharmaceutical compositions described herein can be used in combination with other drugs.

In some embodiments, provided herein are pharmaceutical compositions (e.g., pharmaceutical compositions described elsewhere herein) for use in a method described herein. In some embodiments, provided herein are compounds (e.g., a compound provided herein such as compound of Table 1 or Table 2, such as Compound 1a) for use in a method described herein.

In some embodiments, a compound provided herein is administered to the subject in an amount of about 5-50 mg per dose. In some embodiments, a compound provided herein is administered to the subject in an amount of about 1-10 mg per dose. In some embodiments, a compound provided herein is administered to the subject in an amount of about 10-25 mg per dose. In some embodiments, a compound provided herein is administered to the subject in an amount of about 25-35 mg per dose. In some embodiments, a compound provided herein is administered to the subject in an amount of about 35-50 mg per dose. In some embodiments, a compound provided herein is administered to the subject in an amount of about 50-200 mg per dose. In some embodiments, a compound provided herein is administered to the subject in an amount of about 5 mg, about 20 mg, about 25 mg, about 30 mg, about 35 mg, about 40 mg, or about 50 mg per dose. In some embodiments, a compound provided herein is administered to the subject in an amount of about 50 mg per dose. In some embodiments, a compound provided herein is administered to the subject in an amount of about 30 mg per dose. In some embodiments, a compound provided herein is administered to the subject in an amount of about 25 mg per dose. In some embodiments, a compound provided herein is administered to the subject in an amount of about 5 mg per dose. In some embodiments, the subject is a horse. In some embodiments, the subject is a horse and the disease is equine metabolic syndrome. In some embodiments, the subject is a dog. In some embodiments, the subject is a dog and the disease is cancer.

In some embodiments, a compound provided herein is administered to the subject in an amount of about 0.01-25 mg/kg per dose. In some embodiments, a compound provided herein is administered to the subject in an amount of about 0.02-0.10 mg/kg per dose. In some embodiments, a compound provided herein is administered to the subject in an amount of about 0.02 mg/kg, about 0.03 mg/kg, about 0.04 mg/kg, about 0.05 mg/kg, about 0.06 mg/kg, about 0.07 mg/kg, or about 0.08 mg/kg per dose. In some embodiments, a compound provided herein is administered to the subject in an amount of about 0.05 mg/kg per dose. In some embodiments, a compound provided herein is administered to the subject in an amount of about 0.1-10 mg/kg per dose. In some embodiments, a compound provided herein is administered to the subject in an amount of about 0.1 mg/kg, about 0.5 mg/kg, about 2.5 mg/kg, or about 5 mg/kg per dose. In some embodiments, a compound provided herein is administered to the subject in an amount of about 0.5 mg/kg per dose. In some embodiments, a compound provided herein is administered to the subject in an amount of about 2.5 mg/kg per dose. In some embodiments, a compound provided herein is administered to the subject in an amount of about 5 mg/kg per dose. In some embodiments, the subject is a horse. In some embodiments, the subject is a horse and the disease is equine metabolic syndrome. In some embodiments, the subject is a dog. In some embodiments, the subject is a dog and the disease is cancer. In some embodiments, the subject is a dog and the condition is obesity.

In some embodiments, a compound provided herein is administered to the subject in a single dose. In some embodiments, a compound provided herein is administered to the subject in multiple doses. In some embodiments, a compound provided herein is administered to the subject every 2-6 weeks. In some embodiments, a compound provided herein is administered to the subject in a single dose every 2-6 weeks. In some embodiments, a compound provided herein is administered to the subject in a single dose every 4 weeks.

Methods of Manufacture

In some embodiments, provided herein are methods of manufacturing any of the compounds provided herein (e.g., such as described in Example 1). In some embodiments, the methods comprise providing a compound of Formula (X) or a stereoisomer thereof:

Formula (X)

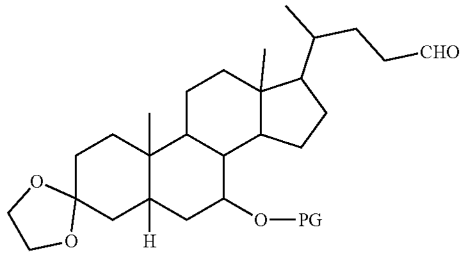

wherein PG is an alcohol protecting group (e.g., a benzoyl group).

In some embodiments, the method comprises contacting the compound of Formula (X) with a reagent to provide a compound of Formula (Z):

Formula (Z)

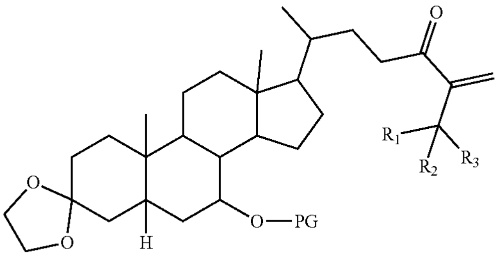

wherein PG is an alcohol protecting group, and the definitions of $R_1$, $R_2$, and $R_3$ are as described in Formula (I).

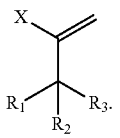

In some embodiments, the reagent is In some embodiments, X is a halogen. In some embodiments, X is Cl, F, or Br. In some embodiments, X is Cl or Br. In some embodiments, X is Br. In some embodiments, $R_1$, $R_2$, and $R_3$ are as described elsewhere herein.

In some embodiments, the method comprises reducing, deprotecting, and sulfonylating the compound of Formula (Z) such as to provide a compound of Formula (W):

Formula (W)

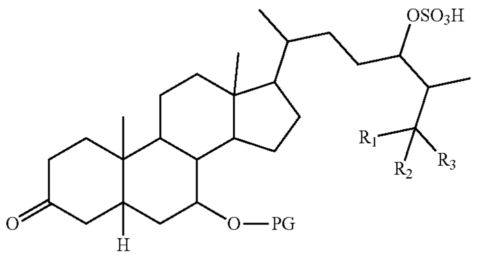

wherein PG is an alcohol protecting group, and the definitions of $R_1$, $R_2$, and $R_3$ are as described in Formula (I).

In some embodiments, PG is acetyl (Ac), benzoyl (Bz), pivaloyl (Piv), or a benzyloxycarbonyl group (CBz).

In some embodiments, PG is Bz.

In some embodiments, the method comprises reducing the compound of Formula (Z). In some embodiments, the reducing comprises stereospecific reduction. The stereospecific reduction may provide the desired stereochemistry of carbons C24 and C25, as described elsewhere herein. The stereochemistry of carbons C24 and C25 may have an impact on the resulting pharmacological properties of the compound. In some embodiments, the reducing comprises the use of a chiral reducing reagent, such as any suitable chiral reducing reagent. In some embodiments, the chiral reducing reagent is (R,R)-Ts-DENEB.

In some embodiments, the method comprises deprotecting the compound of Formula (Z), such as deprotecting to remove the acetal protecting group. In some embodiments, the deprotecting comprises use of an acid. In some embodiments, the acid is hydrochloric acid, sulfuric acid, hydrobromic acid, perchloric acid, or any other suitable acid. In some embodiments, the acid is used in any suitable concentration, such as 0.1 M, 0.2 M, 0.4 M, 0.6 M, 1 M. 2 M. 4 M. 8 M, or 10 M. In some embodiments, the acid is 1 M HCl.

In some embodiments, the method comprises sulfonylating the compound of Formula (Z). Sulfonylation may be completed using any suitable reagent, such as pyridine·$SO_3$.

In some embodiments, the method comprises contacting the compound of Formula (W) with a protected spermine and deprotecting to provide the compound provided herein. In some embodiments, the method comprises contacting the compound of Formula (W) with a protected spermine. In some embodiments, the method comprises reacting the compound of Formula (W) with a spermine. In some embodiments, the spermine is protected. In some embodiments, the method further comprises deprotecting the spermine.

In some embodiments, the spermine may be protected with any suitable group, such as benzyloxycarbonyl (CBz). In some embodiments, the protected spermine may be spermine-CBZ.

In some embodiments, the method comprises deprotecting the compound (e.g., after addition of the spermine). In some embodiments, the method comprises removing the PG group. In some embodiments, the method comprises replacing the PG group with a hydrogen. The deprotecting may comprise use of a base. In some embodiments, the base is sodium hydroxide, calcium hydroxide, potassium hydroxide, or lithium hydroxide. In some embodiments, the base is potassium hydroxide.

In some embodiments, the resulting product is purified to provide the resulting compound provided herein.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein may be employed in practicing the invention.

EXAMPLES

Example 1: Preparation of Compound 1a

Figure 2:
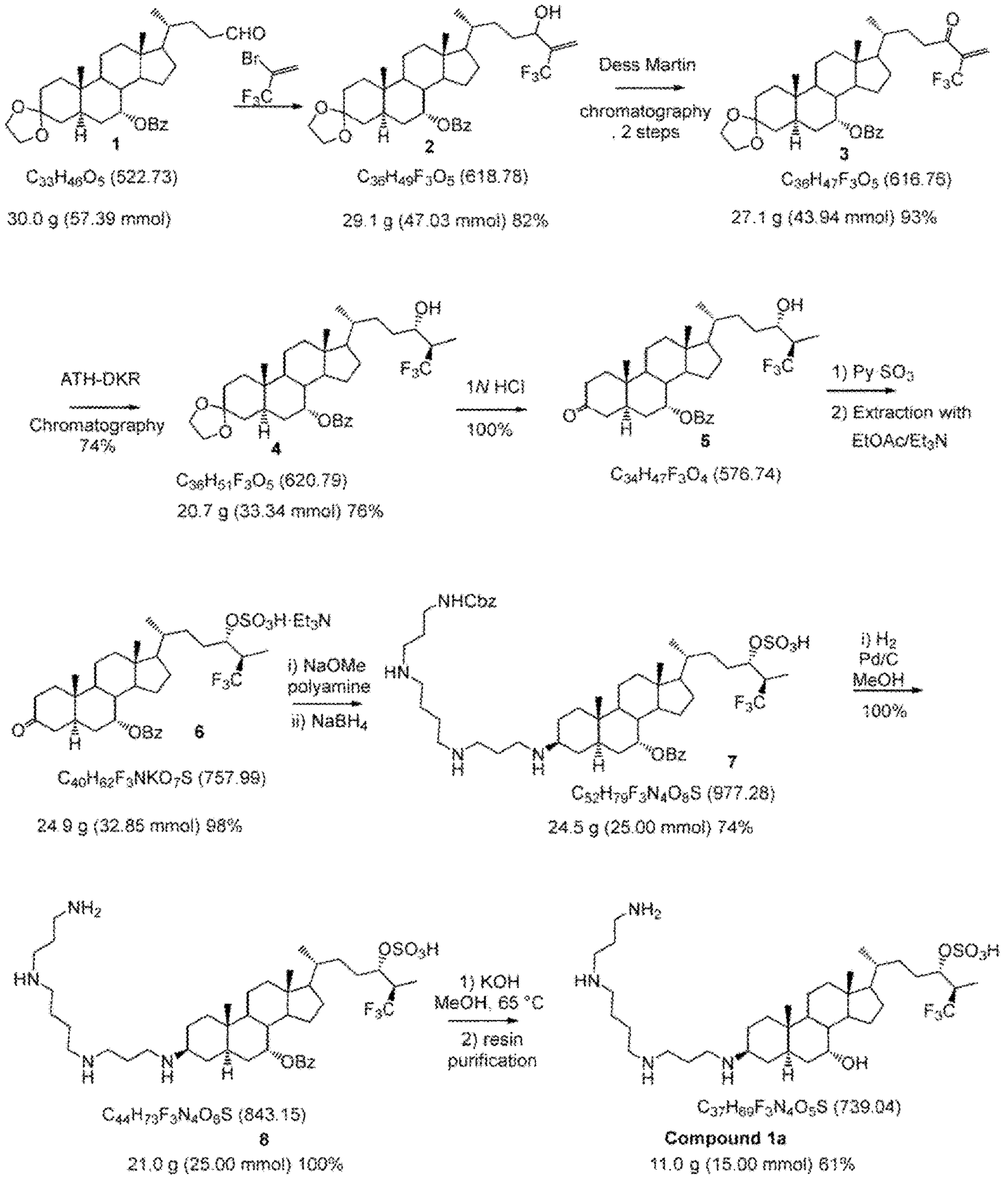
FIG. 2 show an illustrative scheme for the preparation of a compound provided herein.

Compound 1a was prepared as described in FIG. 2. As shown in Scheme 1, a Grignard reaction was performed using 3.0 equivalents of i-PrMgCl·LiCl and 3.3 equivalents of the bromide and conducted in an EZ Max reactor. The reaction products were chromatographed to provide a total of 29.1 g of $CF_3$-olefin (2).

Scheme 1

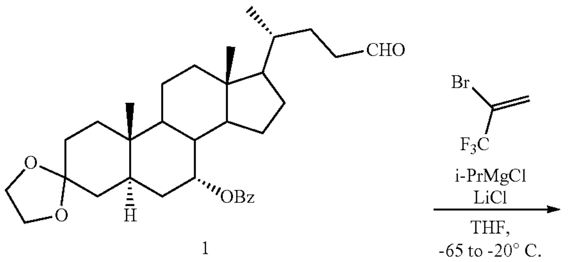

1
$C_{33}H_{45}O_5$ (522.73)
30 g

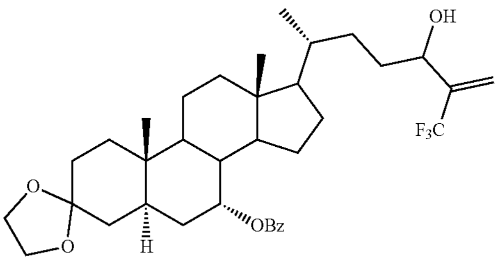

2
$C_{36}H_{49}F_3O_5$ (618.78)
29.1 g (82%)

The allyl alcohol (2) was oxidized to the corresponding enone (3) by Dess Martin Periodinane (Scheme 2). The reactions were carried out in two batches (5 g and 24.1 g), which were combined for the subsequent work up and purification.

Scheme 2

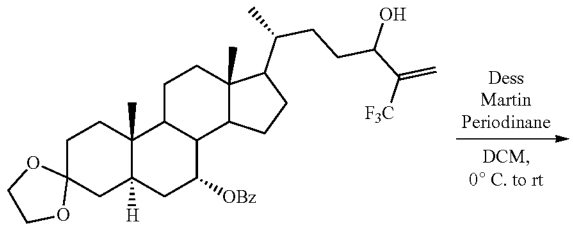

2
$C_{36}H_{49}F_3O_5$ (618.78)
29.1 g (82%)

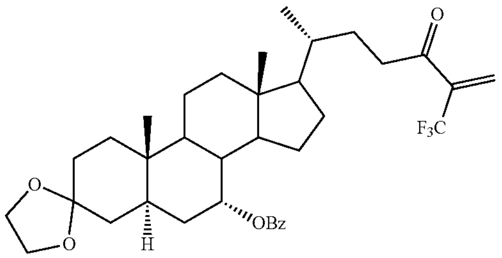

3
$C_{35}H_{47}F_3O_5$ (616.76)

Stereospecific reduction of the enone (3) was carried out with 4 mol % of (R,R)-Ts-DENEB using $HCO_2H$:$Et_3N$ (5:2) in EtOAc at 40° C. over the weekend (66 h), as shown in Scheme 3. The ratio of four diastereomers was, (24S,25R):(24S,25S):(24R,25S):(24R,25R)=88:6:1:5. The rest of (3) (26.1 g) was reacted under the same conditions. After multiple runs of silica-gel column chromatography, a total of 20.7 g (>95A %) of (24S,25R)-(4) was obtained.

Scheme 3

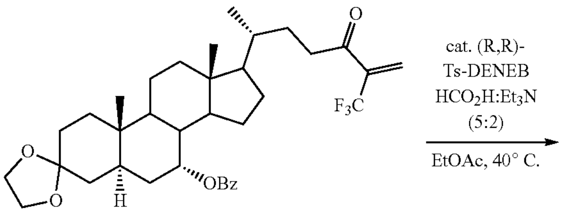

3
$C_{35}H_{47}F_3O_5$ (616.76)
27.1 g (93%)

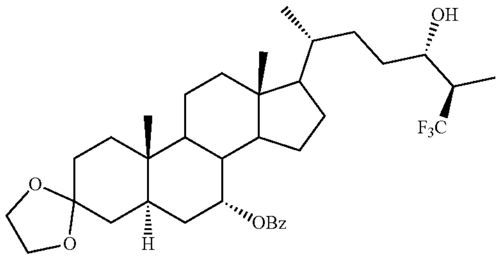

4
$C_{36}H_{51}F_3O_5$ (620.79)

Acetonide deprotection of (4) with 1N HCl was completed to yield (5) (Scheme 4). Crude (5) was azeotropically dried using toluene. Suflonylation of (5) was completed overnight with 2.0 equivalents of pyridine·$SO_3$ (Scheme 4). The resulting product was azeotropically dried with toluene prior to the subsequent reductive amination step.

Scheme 4

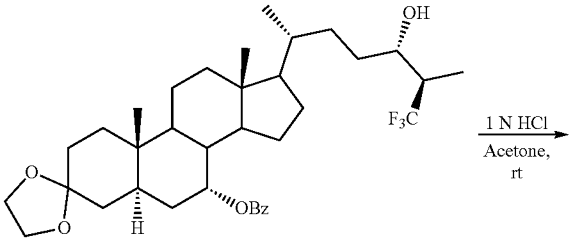

4

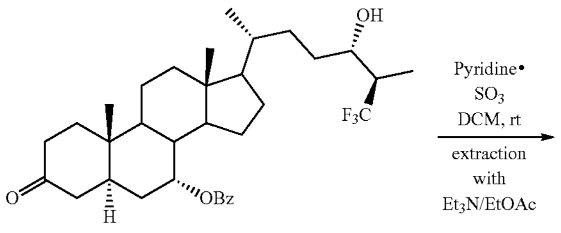

5

-continued

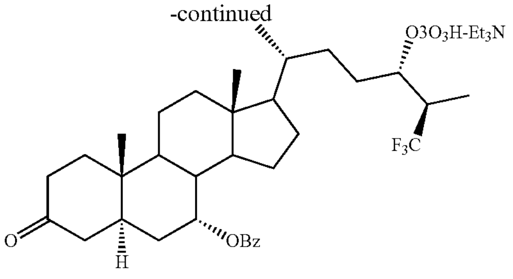

6

The protected polyamine (CBz-spermine) was joined to (6) to yield crude (7), as shown in Scheme 5. NaOMe and MS3A were added in sufficient amounts to push the conversion up to 90A %. After reduction with $NaBH_4$, (7) resulted in 86A %. The ratio of B: a was 92:8. It contained ca 11A % of C3-OH. Reaction mixture was filtered over Celite pad to remove molecular sieves. The product was eluted from the filter cake with MeOH. To the filtrate was added water (300 mL) and it was concentrated to remove MeOH. Celite was added to the residual aqueous mixture. It was loaded over a pad of Celite (20 g) and the filter cake was rinsed with water (500 mL×3). All filtrate was checked by LCMS and no (7) was observed. The filter cake was rinsed with MeOH (500 mL×3). The filtrate contained (7). Thus, the filter cake was continued to rinse with MeOH while monitoring all filtrates by HPLC. It took an additional 2.5 L of MeOH. The filtrate was concentrated by evaporation to give 70 grams of wet residue.

Scheme 5

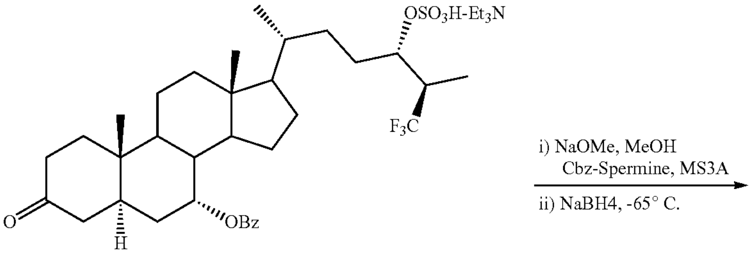

6

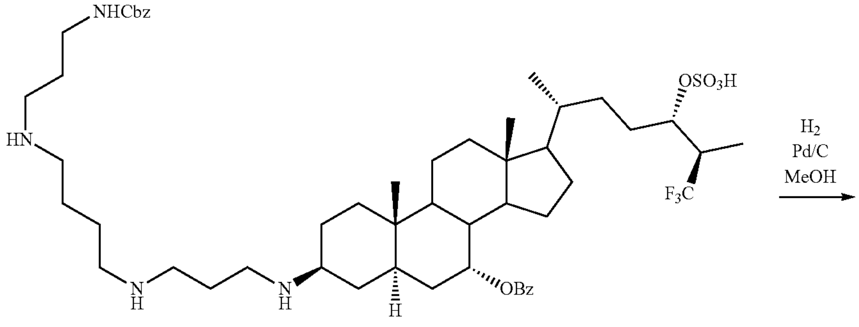

7

Crude (7) material was diluted with MeOH (300 mL) to form a homogeneous clear solution (small amount of insoluble white solid was observed). The solution was hydrogenated with 10% Pd/C (3.0 g). The reaction was completed after overnight. The catalyst was removed by filtration over a Celite pad. Concentration of the filtrate gave 39 grams of (8) in the form of a light-yellow foam. HPLC indicated it contained ca 20A % of C3-OH. Crude (8) was dissolved in isopropanol and KOH was added as a 15% solution in water (Scheme 6). The reaction was maintained at 76° C. overnight. 2-butanol was added to create two phases. The aqueous phase contained the desired product.

Scheme 6

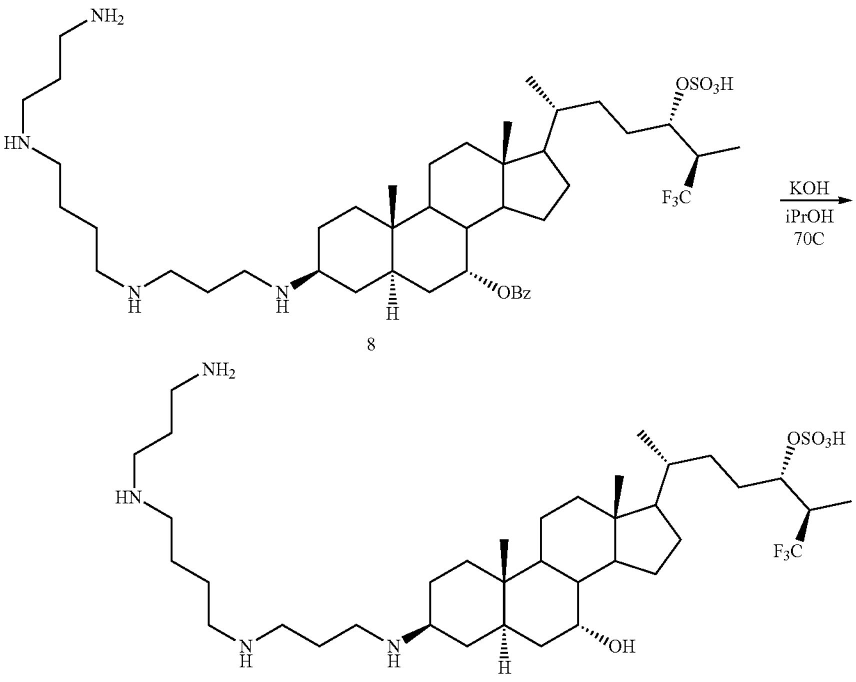

8

Formula Ia
Chemical Formula: $C_{33}H_{69}F_3N_4O_3S$
Molecular Weight: 739.04

To the resulting solution at 50° C. was added 1M $H_3PO_4$ solution until mixture turned to pH=6. The mixture was cooled to ambient temperature and the supernatant was removed. LCMS indicated that trace amounts of product in the supernatant. A sticky solid remained after the supernatant was removed. Most of benzoic acid and possibly C3-OH were rejected to this supernatant. The residual solids were triturated in MeOH and the resulting solid was filtered. The resulting Compound 1a was approximately 95% pure, with the (7) benzoate and the (3a) isomer as the primary contaminants.

Example 2: Preparation of a Subcutaneous Formulation of Compound 1a Using Hydrochloride Salt 34.5 mg of Compound 1a-3HCl was dissolved into 2 mL distilled water. 600 mg of 2 hydroxypropyl B-cyclodextrin was added and brought into solution with gentle stirring. Water was added to 6 mL, pH was adjusted to between 7.0-7.5 with 15 μL 0.5 M Sodium triphosphate. 2-hydroxypropyl β-cyclodextrin was added to maintain the solubility of Compound 1a in the presence of phosphate buffer. The final concentration is Compound 1a, 5 mg/mL, 10% 2-hydroxypropyl β-cyclodextrin, phosphate to bring the pH to 7.0-7.5. The solution was sterilized by filtration through a 0.2 μm cellulose acetate filter into a 10 mL sterile vial.

Example 3: Preparation of a Subcutaneous Formulation of Compound 1a Using the Freebase 35 mg of Compound 1a as the free base placed into a 10 mL vial. 350 mg of 2-hydroxypropyl B-cyclodextrin powder was then added to the vial. 2 mL of distilled water was added, and the solids were brought into solution. 2-hydroxypropyl B-cyclodextrin was used to solubilize the water insoluble freebase. The pH was adjusted to 7.0 by addition of IM phosphoric acid. Water was added to bring the final volume to 3.5 mL. The solution was sterilized by filtration through a 0.2 μM cellulose acetate filter into a 10 mL sterile vial.

Example 4: XRPD

Figure 3:
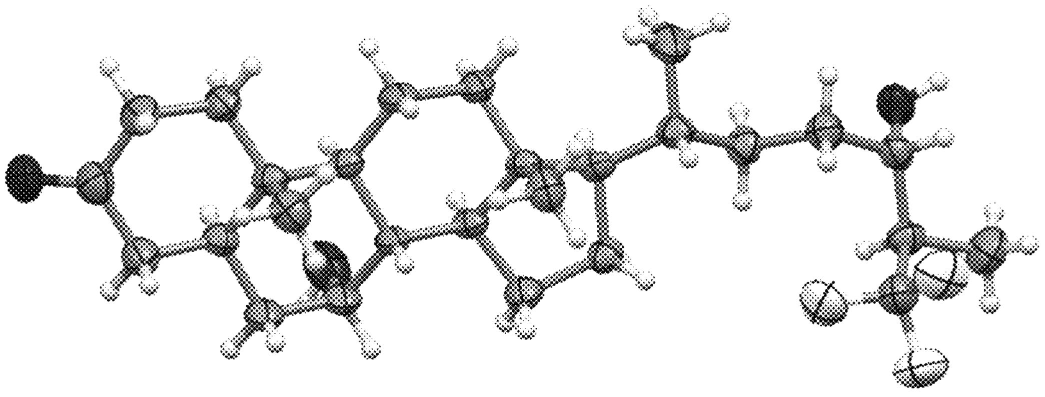
FIG. 3 shows an ORTEP drawing of the X-ray structure determined using a plate-like crystal. The absolute stereochemistry of carbon atom C24 and C25 was established based on known stereochemistry of other six chiral centers in the molecule.

The absolute stereochemical structure of the C24 and C25 chiral centers of Compound 1a was determined indirectly by X-Ray diffraction of crystals of the 3 keto des-benzoate intermediate, as shown in FIG. 3.

FIG. 3 shows an ORTEP drawing of the X-ray structure determined using a plate-like crystal. The absolute stereochemistry of carbon atom C24 and C25 was established based on known stereochemistry of other six chiral centers in the molecule.

The CF3 group is oriented in the R configuration and the C24 sulfate is oriented in the S configuration, as per the naming convention described previously.

Figure 4:
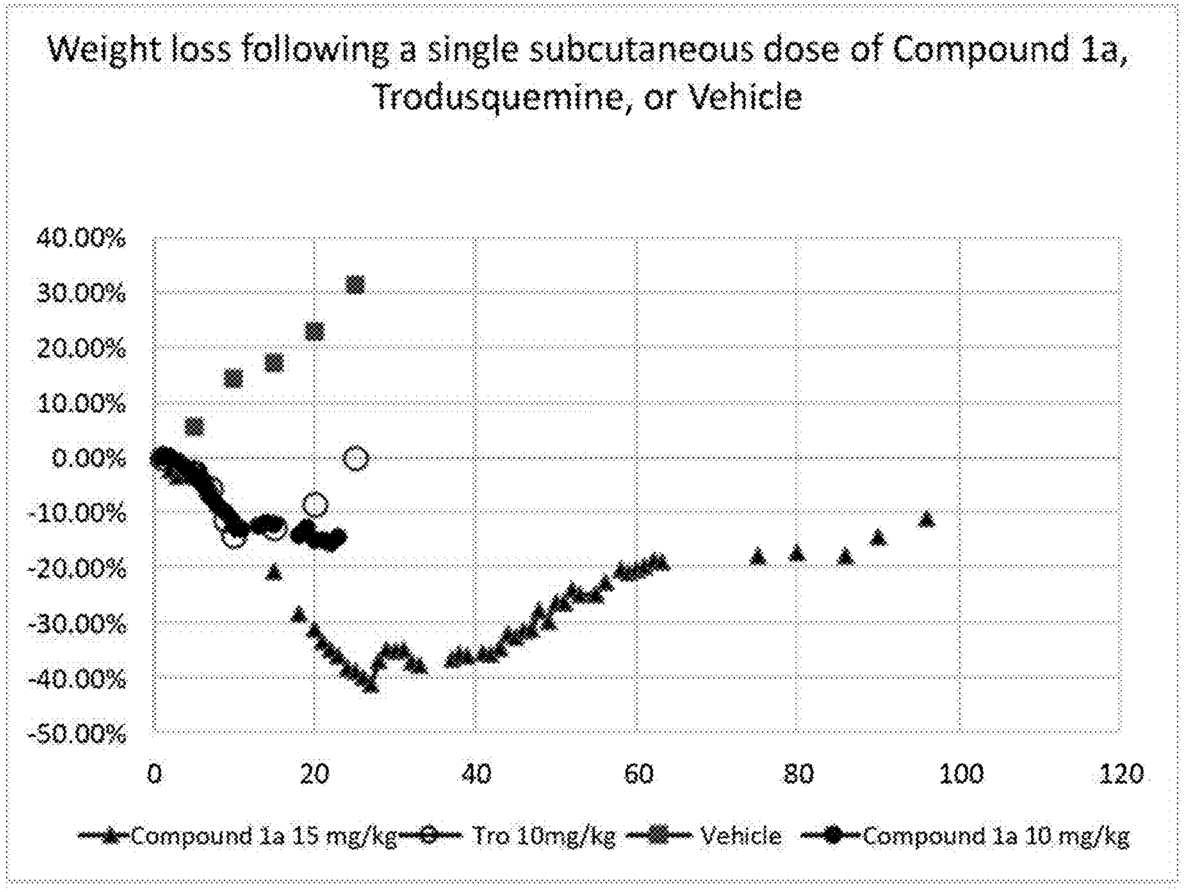
FIG. 4 shows the dose of effect of a single subcutaneous of a compound provided herein on weight loss in male rats compared to Trodusquemine and Vehicle.

Example 5: Compound 1a Exhibits an Extended Pharmacodynamic Effect Compared with Trodusquemine in Male Rats Single doses of Compound 1a. Trodusquemine. or Vehicle were administered to male Sprague Dawley rats on Day 1. Compound 1a and Trodusquemine were administered subcutaneously in the formulation described in Example 3. Compound 1a was administered at 10 mg/kg, or 15 mg/kg to individual rats. Trodusquemine was administered at a dose of 10 mg/kg. Vehicle was the formulation without the aminosterol. Vehicle treated rats (N=10) gained weight progressively. Rats treated with Trodusquemine (N=10) lost about 15% of their initial weight by day 10, reaching a nadir, after which time weight progressively increased, returning to initial weight by about 3 weeks after initial dosing. In contrast, rats treated with Compound 1a at 10 mg/kg reached a nadir in body weight by around day 25 and recovered body weight at a rate that predicted full recovery by around day 45-50, or 1.5 months following the initial dose. Rats treated with a slightly higher dose (15 mg/kg) reached a nadir of body weight of about 40% initial weight by about three weeks. Weight then progressively increased such that by three months following dosing the animals were still 10% below their initial body weights (FIG. 4).

These data demonstrate that the compounds disclosed herein extend the duration of the pharmacodynamic behavior of Trodusquemine.

Example 6: Compound 1a Exhibits an Extended Pharmacodynamic Effect Compared with Trodusquemine in Female Rats Single doses of Compound 1a or Trodusquemine were administered to female Sprague Dawley rats on Day 1. Compound 1a and Trodusquemine were administered subcutaneously using the formulation described in Example 2. Compound 1a was administered in an amount of 10 mg/kg to individual rats. Trodusquemine was administered at a dose of 10 mg/kg.

Figure 5:
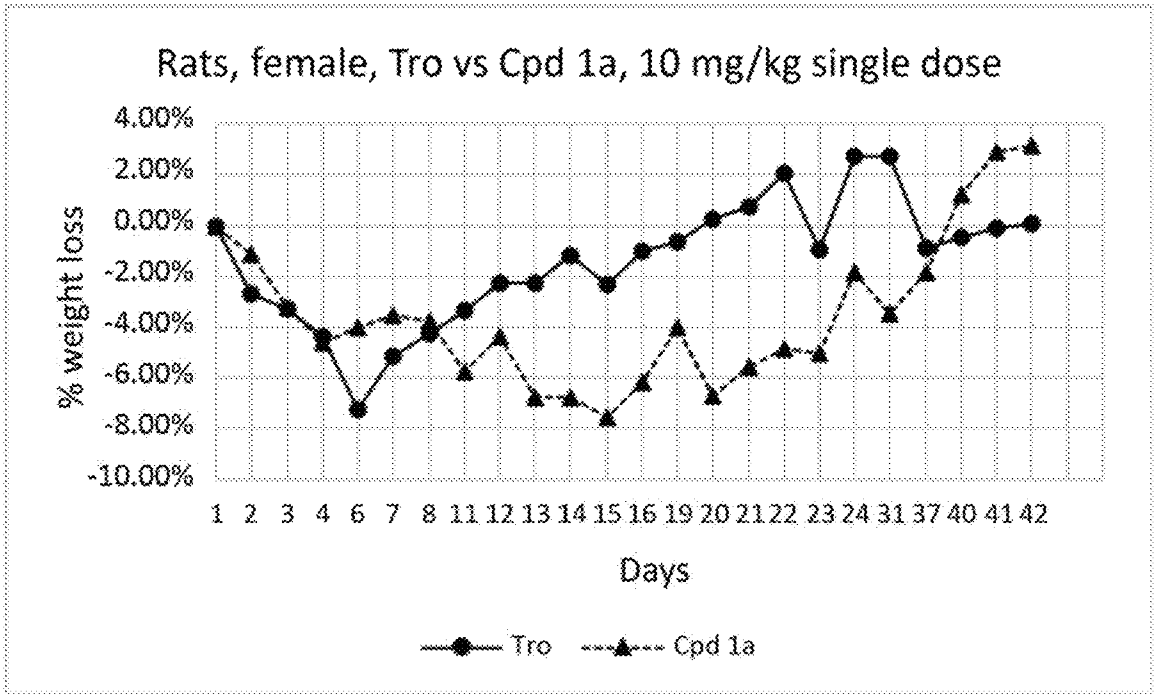
FIG. 5 shows the dose of effect of a single subcutaneous of a compound provided herein on weight loss in female rats compared to Trodusquemine.

The pharmacodynamics with respect to weight loss of Trodusquemine and Compound 1a exhibited significant differences (FIG. 5). The nadir in weight loss following treatment with Trodusquemine occurred about 5-6 days after dosing, followed by a progressive recovery of weight. Full weight recovery occurred at day 20. In contrast, the nadir in weight loss following administration of Compound 1a occurred around day 19, with full recovery observed around day 38. This example demonstrates that Compound 1a exhibits a duration of the pharmacodynamic effect (weight loss) at least 2-fold that of Trodusquemine.

Figure 6A:
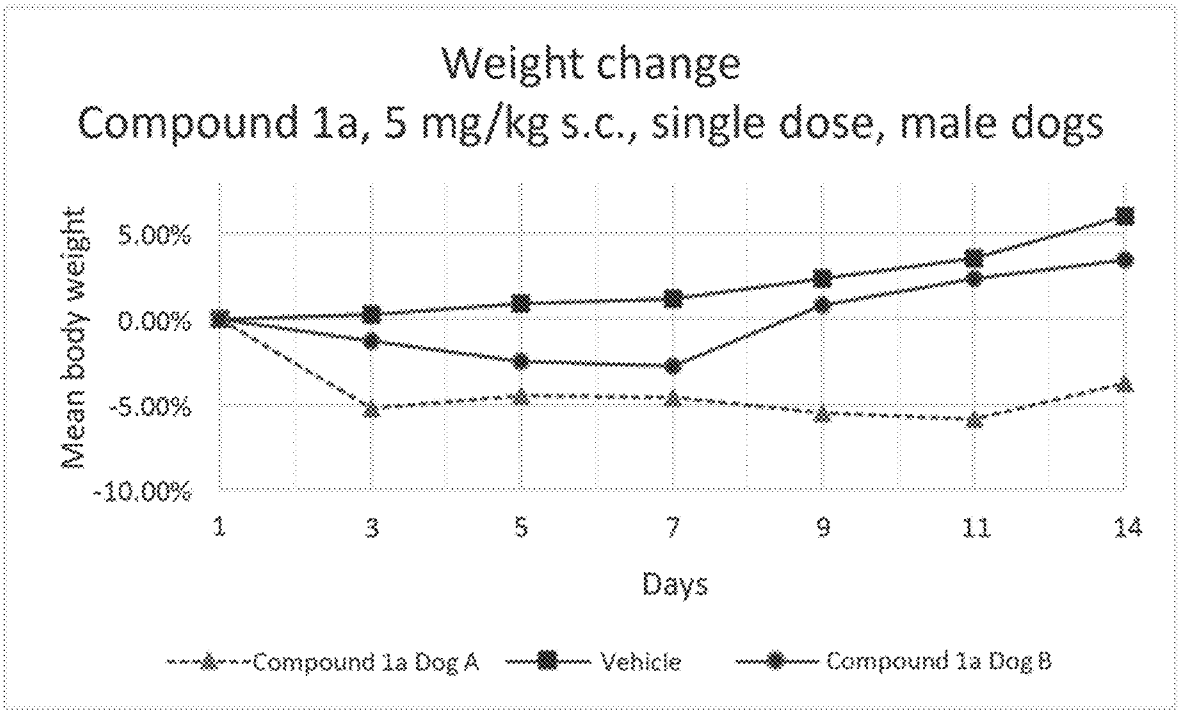
FIG. 6A shows mean body weight change after subcutaneous administration of a compound provided herein in dogs.
Figure 6B:
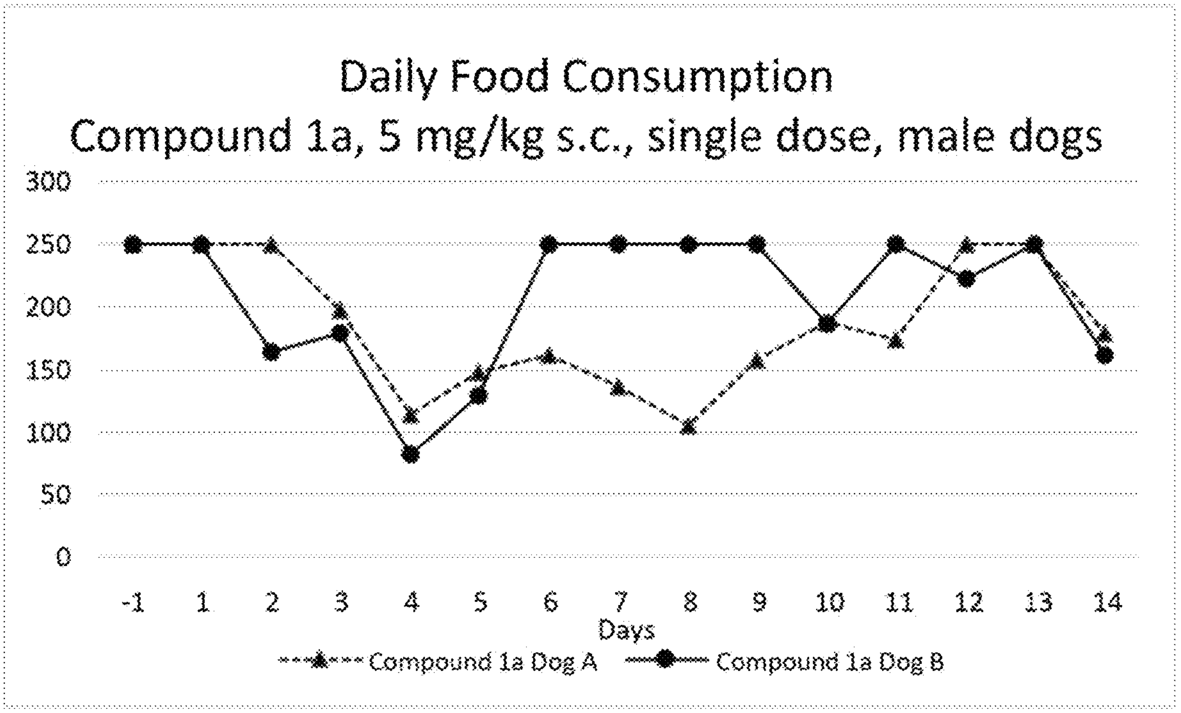
FIG. 6B shows daily food consumption after subcutaneous administration of a compound provided herein in dogs.

Example 7: Single Dose of Compound 1a Reduces Food Intake and Body Weight in Lean Dogs Single doses of Compound 1a (5 mg/kg) in the formulation described in Example 3 or vehicle were administered subcutaneously to 10-11 month old male beagle dogs. The animals were followed for 14 days post dosing. Food intake was monitored daily. Within 1-2 days of dosing, both dogs reduced their daily food intake and exhibited a corresponding decrease in body weight (FIG. 6A and FIG. 6B). One dog exhibited a sustained weight loss of about 5% over the 14 day observation period, while the other reached a nadir in body weight of about 3% by day 7 with gradual recovery (FIG. 6A). Animals receiving vehicle gained about 5% body weight over the observation period. These data demonstrate that a single dose of Compound 1a exhibits an extended pharmacodynamic effect exceeding 1-2 weeks.

Example 8: Pharmacokinetic Analysis of Compound 1a

The concentration of Compound 1a was measured over time following the initial administration to the dogs studied in Example 7 in order to establish the pharmacokinetic parameters associated with Compound 1a. The mean plasma half-life was about 24 hours (23.55 hr).

Figure 7:
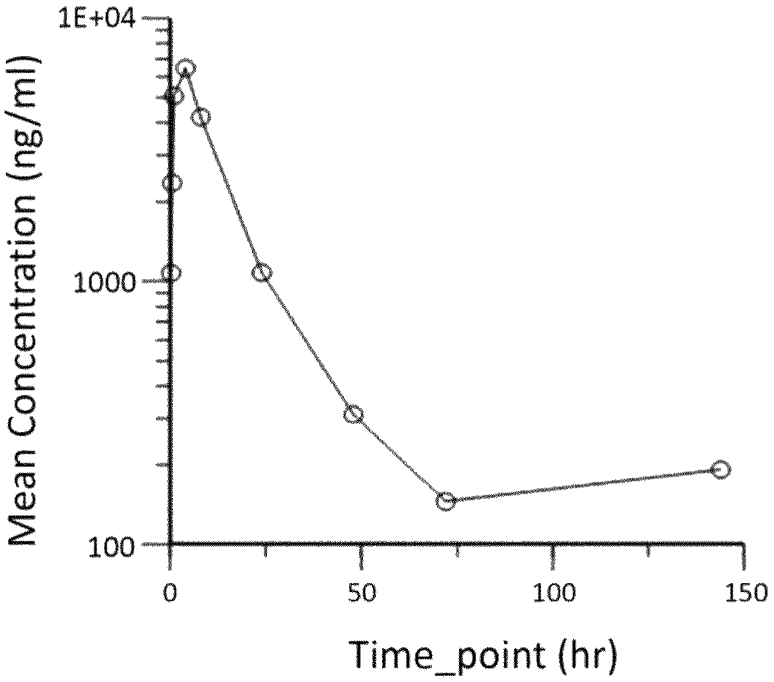
FIG. 7 shows the blood levels of a compound provided herein (Compound 1a) in dogs following a subcutaneous dose of 5 mg/kg.

A striking feature of the pharmacokinetic analysis is the increase observed in the concentration of circulating Compound 1a at late times (i.e., after 70 hours), reflecting re-equilibration of the compound between the tissues and blood circulation under conditions of slow metabolic clearance (FIG. 7). The PK and pharmacodynamic data together demonstrate that following administration. Compound 1a rapidly distributes from the blood into tissues, from which it is slowly removed by metabolic elimination.

Example 9: Compound 1a Reduces Obesity, Improves Glucose Tolerance and Improves Mobility in Horses Suffering from Equine Metabolic Syndrome Four female Polish Konik horses were administered a single dose of Compound 1a (0.1 mg/kg) in the formulation described in Example 3 via the intravenous route. At 2.5 weeks post-dosing horses 1-3 were administered a second dose of Compound 1a (0.2 mg/kg) by the intravenous route. Each animal had suffered repeated episodes of laminitis, were markedly obese and insulin resistant. The mares were fed exclusively with hay supplemented with a mineral-vitamin mix. Carbohydrates were reduced to a minimum to manage obesity and stabilize blood glucose levels. Hay was provided at 1.5% of body weight daily to promote weight loss and maintain metabolic health.

Figure 8A:
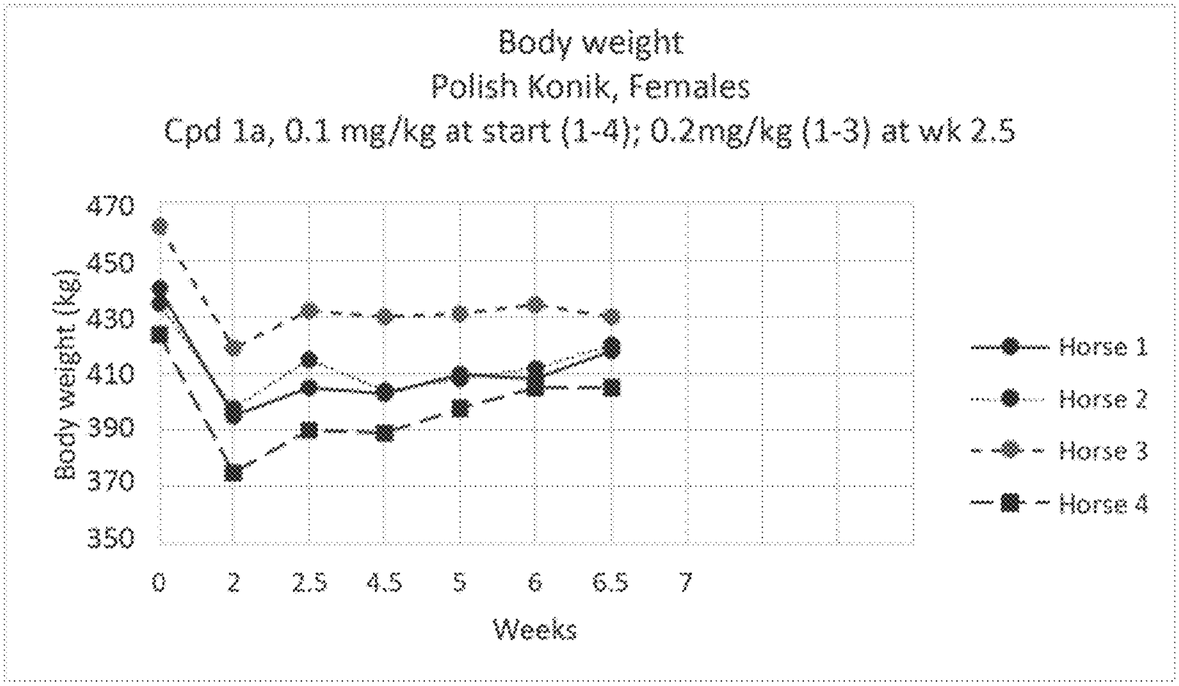
FIG. 8A shows body weight in horses after administration of a compound provided herein.
Figure 8B:
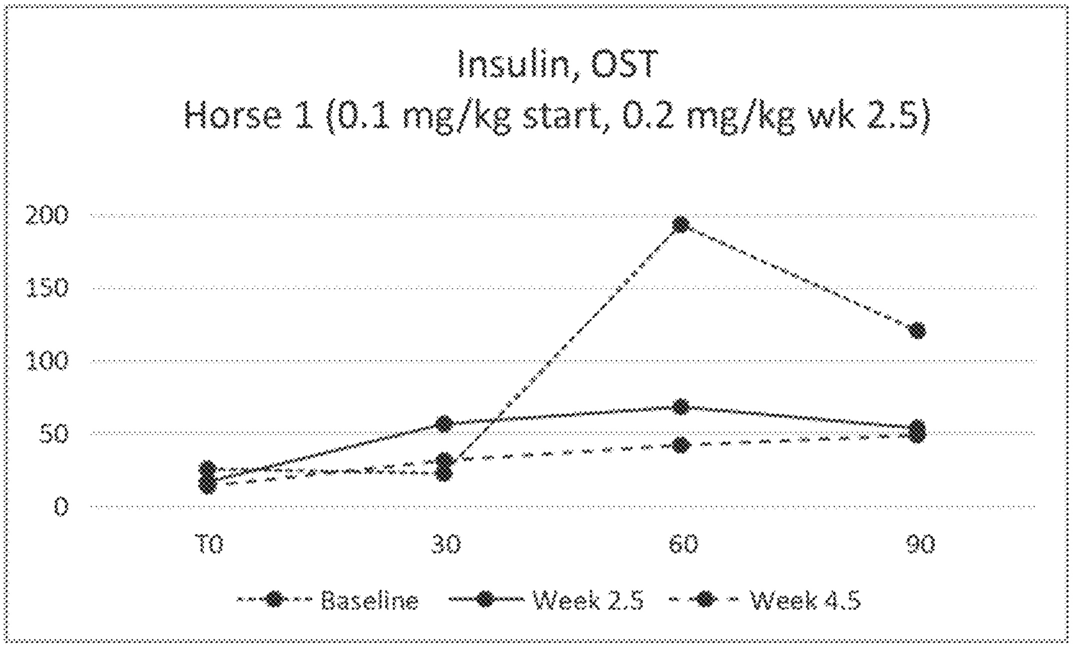
FIG. 8B, FIG. 8C, FIG. 8D, and FIG. 8E show insulin levels in horses after administration of a compound provided herein.
Figure 8C:
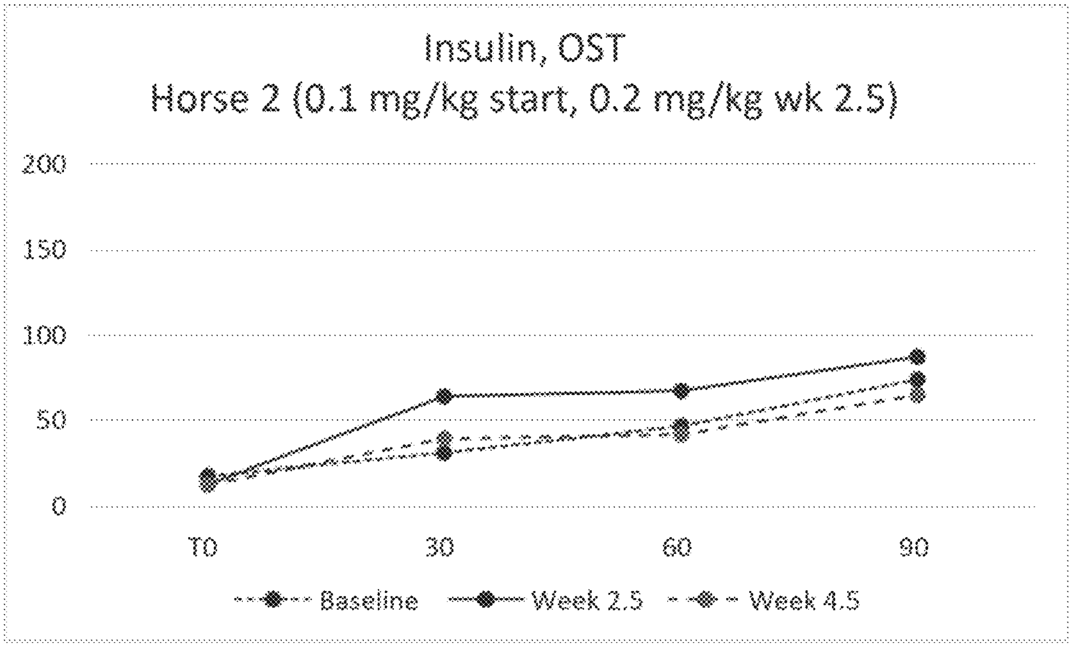
Figure 8D:
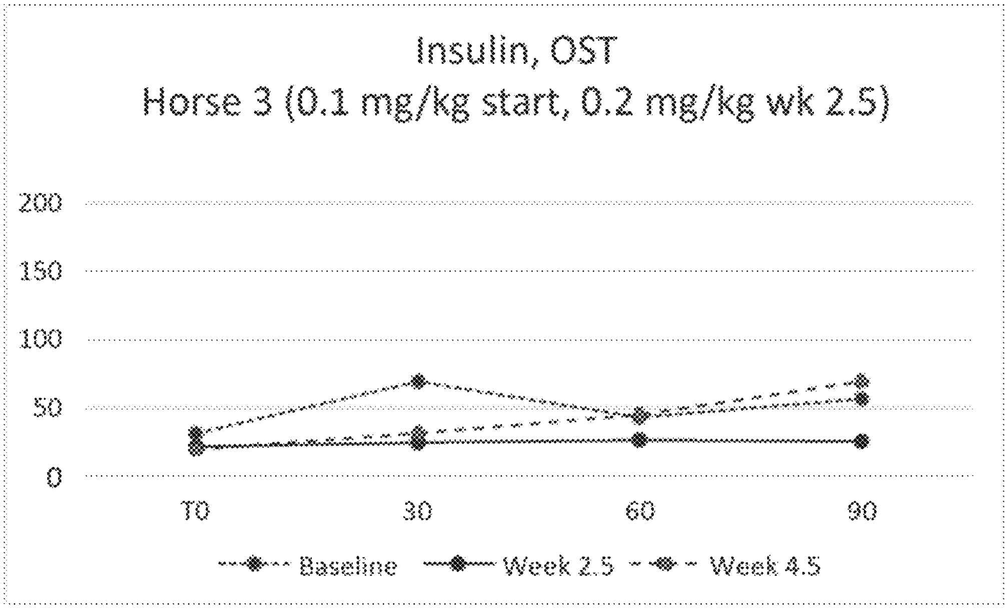
Figure 8E:
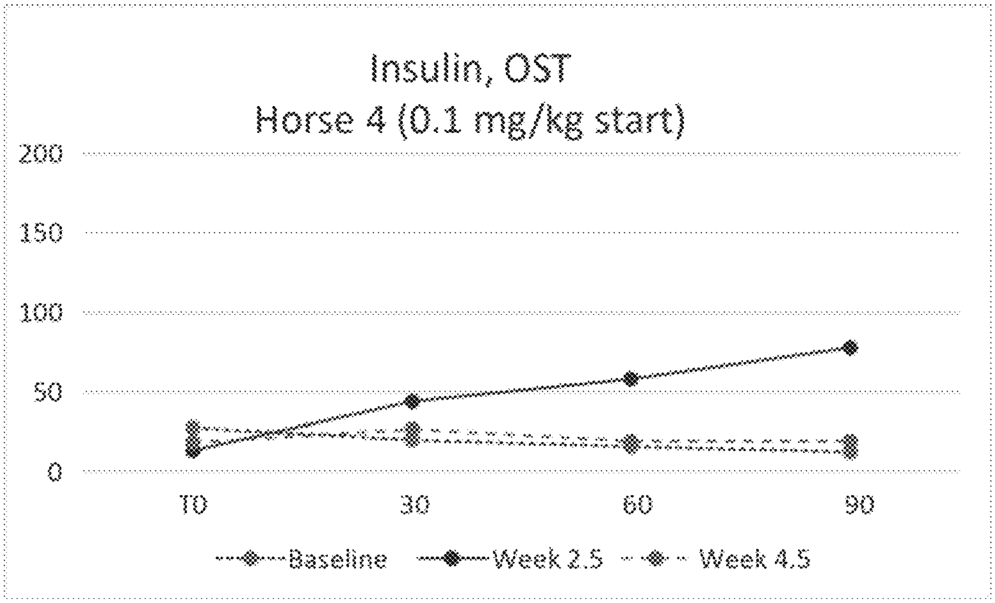
Figure 8F:
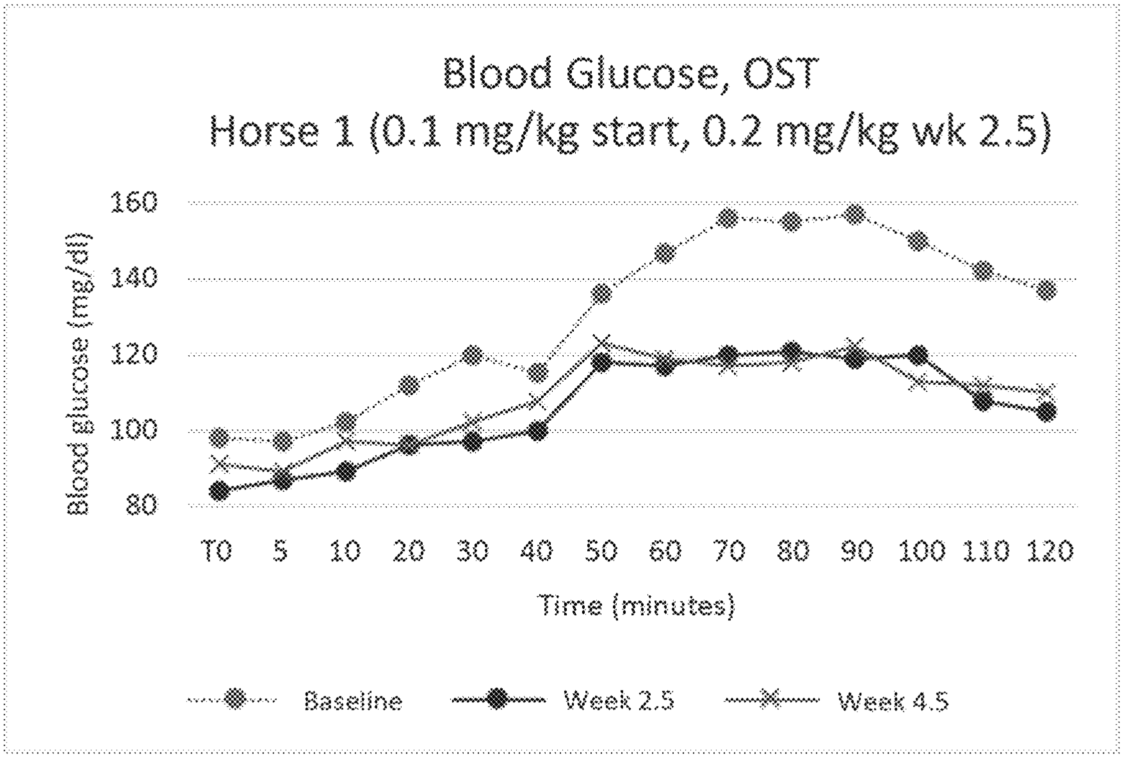
Figure 8G:
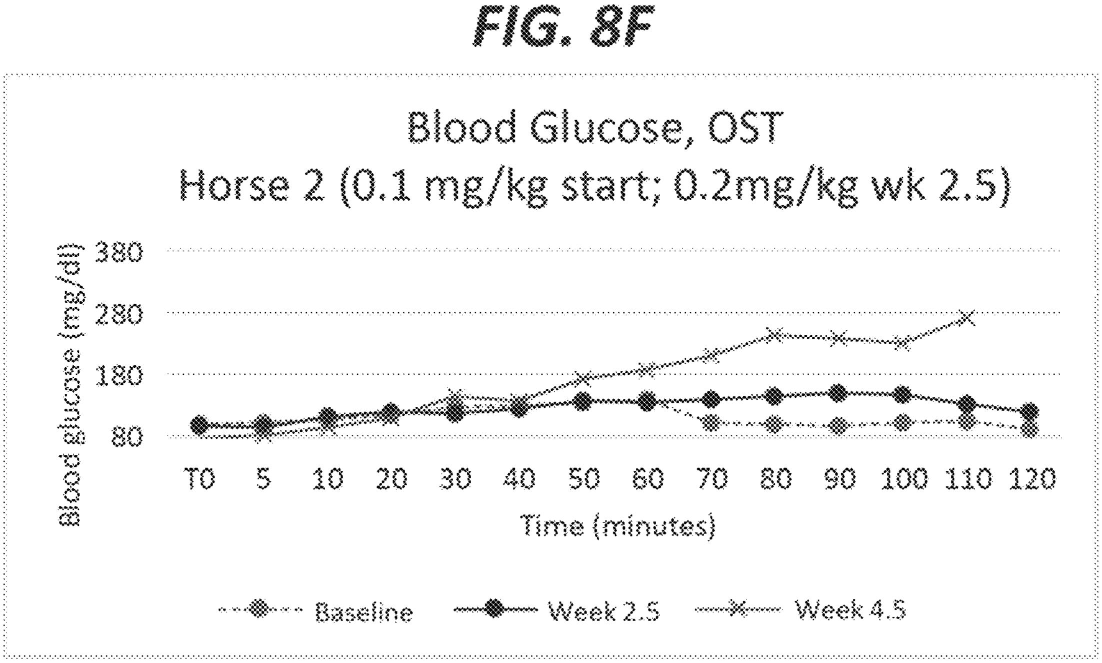
Figure 8J:
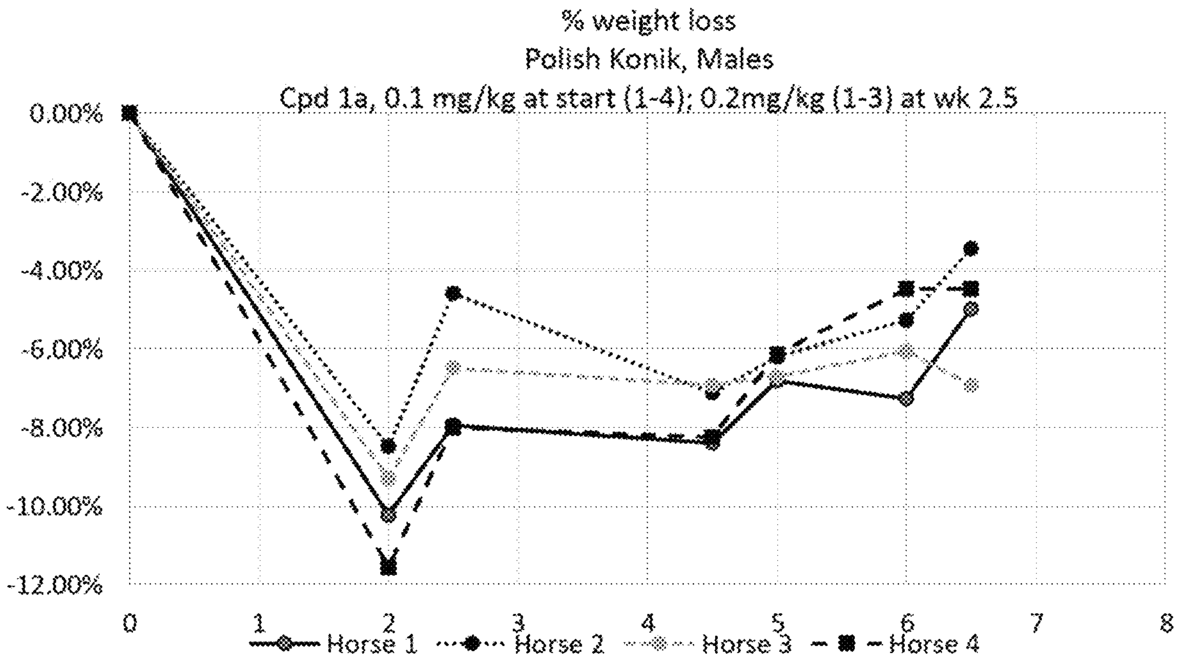
FIG. 8J shows percent weight loss horses after administration of a compound provided herein.

Two and a half weeks post the initial 0.1 mg/kg dose body weights were measured. Each of the horses lost between 8-12% (mean 9.9%) (FIG. 8A, FIG. 8J). Horses 1-3, having received a second administration of Compound 1a maintained reduced body weight of between 5-7% from starting weight for at least 4 weeks following the second administration. Horse 4, having received only a single dose at the start remained about 4% below starting weight at week 6.5, demonstrating the persistence of the pharmacodynamic effect. Weight loss was associated with decreased food intake. An oral sugar test (OST) demonstrated a dramatic improvement in the excursion of blood insulin levels in Horse 1, the only animal of the four exhibiting an abnormal insulin response at baseline (FIGS. 8B-8E). The glycemic response also improved in Horse 1, consistent with reduction in insulin resistance (FIG. 8F-11I). Based on clinical assessment, each of the horses exhibited visibly improved mobility. These data demonstrate that Compound 1a can safely treat obesity and insulin resistance associated with equine metabolic syndrome, along with Improvement in mobility. The pharmacodynamic properties of Compound 1a permit the convenient dosing frequencies of one month or longer.

We claim:

1. A compound having the structure of

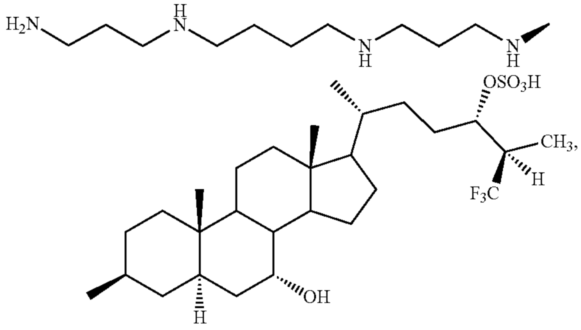

or a pharmaceutically acceptable salt thereof.

2. The compound of claim 1, wherein the compound is:

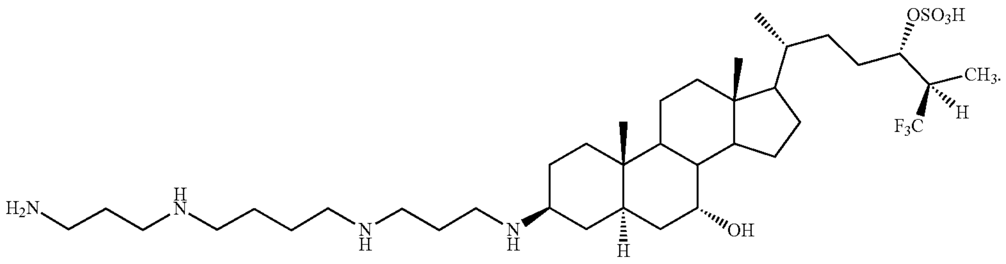

3. A pharmaceutical composition comprising a compound having a structure of

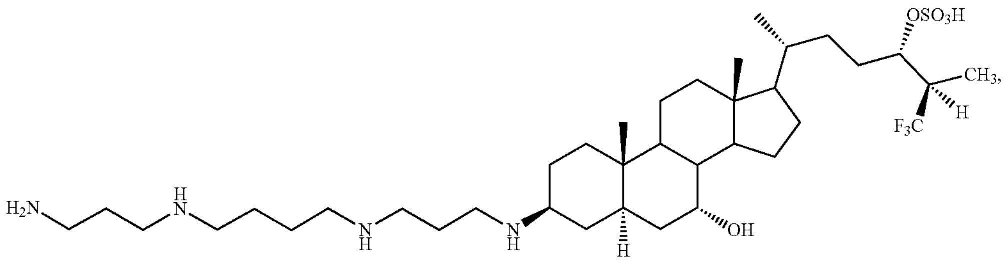

or a pharmaceutically acceptable salt thereof, and a pharmaceutically acceptable excipient.

4. The pharmaceutical composition of claim 3, wherein the pharmaceutical composition comprises the compound, or a pharmaceutically acceptable salt thereof, in an amount of from about 5 mg/mL to about 50 mg/mL.

5. The pharmaceutical composition of claim 4, wherein the pharmaceutical composition comprises:

(a) the compound in an amount of from about 5 mg/mL to about 50 mg/ml;

(b) a solubilizing agent in an amount of from about 80 mg/mL to about 250 mg/ml; and (c) a buffering agent in an amount of from about 20 mM to about 80 mM.

6. The pharmaceutical composition of claim 3, wherein the pharmaceutical composition is formulated for intravenous administration.

* * * * *